United States Patent [19]

Kaneko et al.

[11] 4,427,587

[45] Jan. 24, 1984

[54] TOTAL SYNTHESIS OF ANTITUMOR ANTIBIOTICS BBM-2040A AND BBM-2040B

[75] Inventors: Takushi Kaneko; Henry S. L. Wong, both of Fayetteville, N.Y.

[73] Assignee: Bristol-Myers Company, New York, N.Y.

[21] Appl. No.: 440,779

[22] Filed: Nov. 10, 1982

[51] Int. Cl.$^3$ ............................................. C07D 487/04
[52] U.S. Cl. .............................................. 260/239.3 T
[58] Field of Search ................................. 260/239.3 T

[56] References Cited

PUBLICATIONS

Leimgruber et al., "J. Am. Chem. Soc.", vol. 87, pp. 5793–5795 (1965).
Leimgruber et al., "J. Am. Chem. Soc.", vol. 90, pp. 5641–5643 (1968).
Ishikura et al., J. Chem. Soc., Chem. Commun. (1982), pp. 741–742.
Symposium Papers of 24th Symposium on the Chemistry of Natural Products (Osaka, Oct. 13–16, 1981); Paper No. 72, pp. 552–559.
Takeuchi et al., "J. Antibiotics", vol. 29, No. 1, pp. 93–96 (1976).
Miyamoto et al., "J. Antibiotics", vol. 30, No. 4, pp. 340–343 (1977).
Arima et al., "J. Antibiotics", vol. 25, No. 8, pp. 437–444 (1972).
Kariyone et al., "Chem. Pharm. Bull.", vol. 19, No. 11, pp. 2289–2293 (1971).
"J. Antibiotics", vol. 33, No. 6, pp. 665–667 (1980), Kunimoto et al.
Hurley, "J. Antibiotics", vol. 30, No. 5, pp. 349–370 (1977).
Brazhnikova et al., "J. Antibiotics", vol. 25, No. 11, pp. 668–673 (1972).
Mesentsev, "J. Antibiotics", vol. 27, No. 11, pp. 866–873 (1974).

Primary Examiner—Robert T. Bond
Attorney, Agent, or Firm—David M. Morse

[57] ABSTRACT

A new chemical synthesis of the pyrrolobenzodiazepine antibiotics BBM-2040A and B is disclosed. The disclosed total synthesis uses readily available starting materials and provides a useful alternative to the microbiological procedure previously used to prepare these antibiotics.

19 Claims, 6 Drawing Figures

ULTRAVIOLET ABSORPTION SPECTRUM OF BBM-2040 A

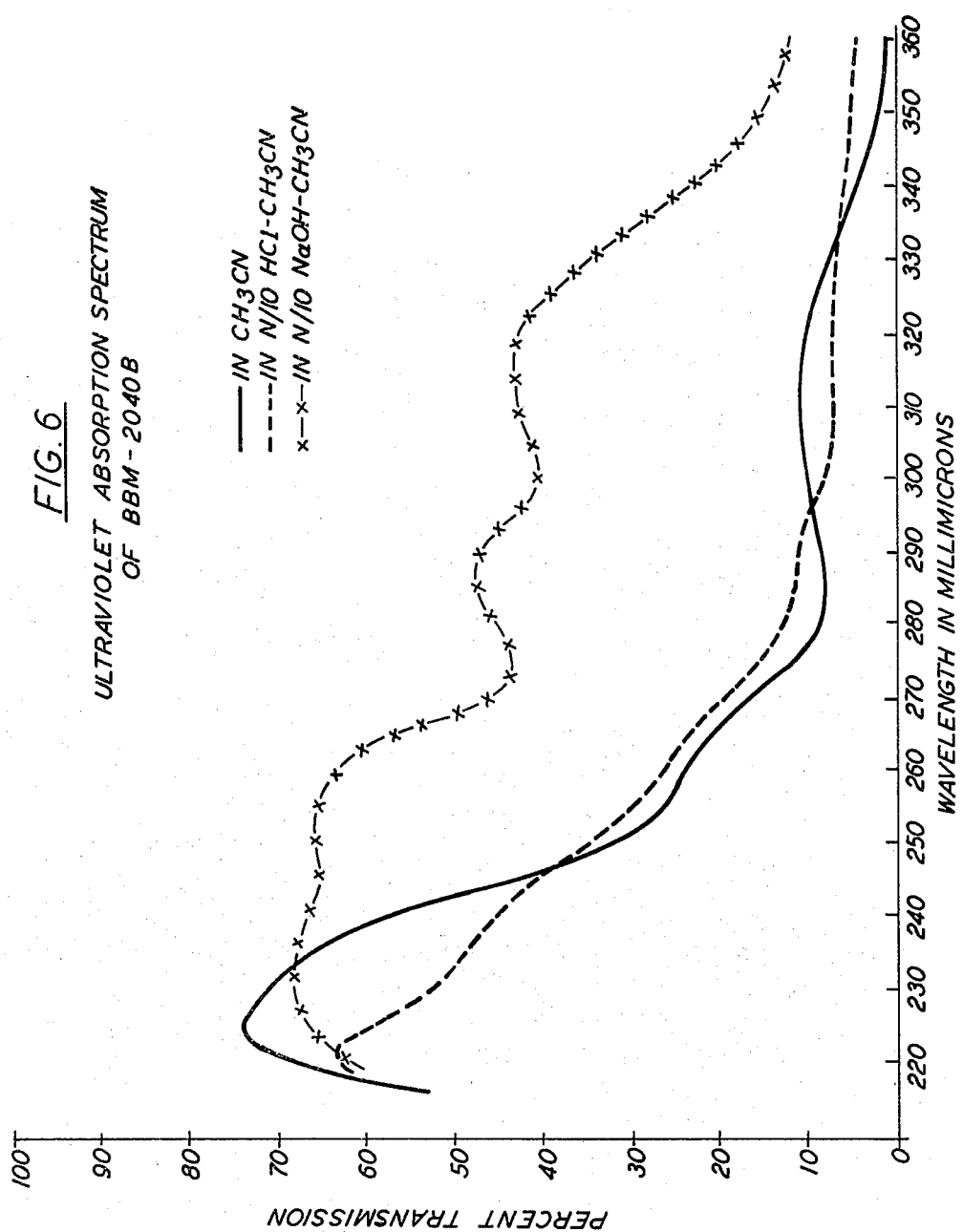

TOTAL SYNTHESIS OF ANTITUMOR ANTIBIOTICS BBM-2040A AND BBM-2040B

BACKGROUND OF THE INVENTION (1) Field of the Invention

This invention relates to a novel chemical synthesis of pyrrolo[2,1-c][1,4]benzodiazepin-5-one antitumor antibiotics previously prepared only by fermentation of a strain of Streptomyces designated Streptomyces sp. strain J576-99 (ATCC 39143).

(2) Description of the Prior Art

The present invention relates to the total synthesis of two pyrrolobenzodiazepine antibiotics having the formula

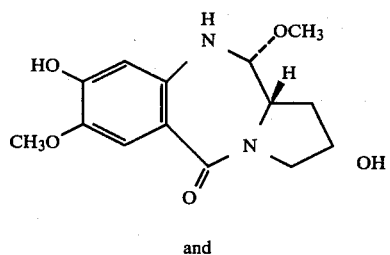

BBM-2040A and

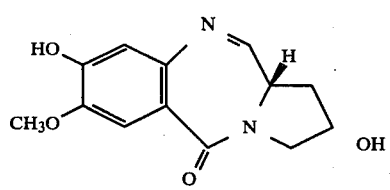

BBM-2040B

These antitumor antibiotics have been disclosed in U.S. application Ser. No. 401,469 filed July 26, 1982 as being isolated from the fermentation broth of Streptomyces sp. strain J576-99 (ATCC 39143). The BBM-2040 antibiotic may be obtained from the fermentation broth in two different forms, A and B, according to the isolation procedure employed. The BBM-2040 antibiotics inhibit the activity of various gram-positive and acid-fast bacteria and also inhibit the growth of mammalian tumors such as P388 leukemia in mice.

The epimers of BBM-2040A and B have been disclosed in *Symposium Papers of the 24th Symposium on the Chemistry of Natural Products* (Osaka, Japan, Oct. 13–16, 1981): Paper #72, pp 552–559. Compounds 31b and 32b in this paper were prepared by a total synthesis procedure and have the structures

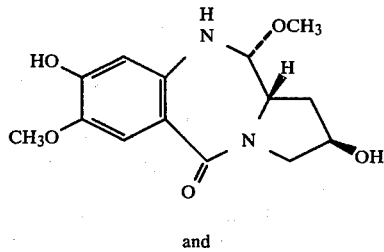

31b and

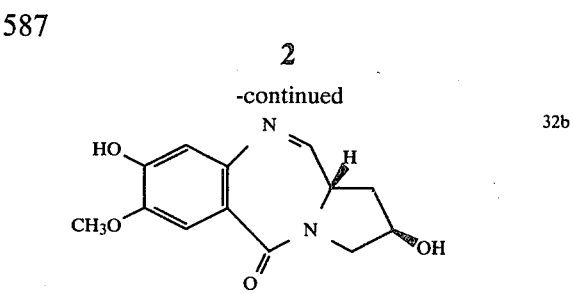

32b

They may be differentiated from BBM-2040A and B in the configuration of the C-2 hydroxy group, i.e. BBM-2040A and B have the C-2 hydroxy group in the α-configuration while the corresponding 31b and 32b diastereoisomers have the β-configuration at the C-2 hydroxy group. It has been found that the β-hydroxy isomers described in the reference are essentially devoid of antitumor activity in the P388 mouse leukemia test while the α-hydroxy isomers have a marked activity against P388 mouse leukemia in this same screening test.

The BBM-2040 antibiotics are members of the anthramycin-neothramycin group of antibiotics. Several members of this group have been disclosed in the scientific literature.

The antitumor antibiotics, neothramycin A and neothramycin B, are disclosed in *J. Antibiotics* 29(1): 93–96 (1976) and *J. Antibiotics* 30(4): 340–343 (1977) ashaving the structures

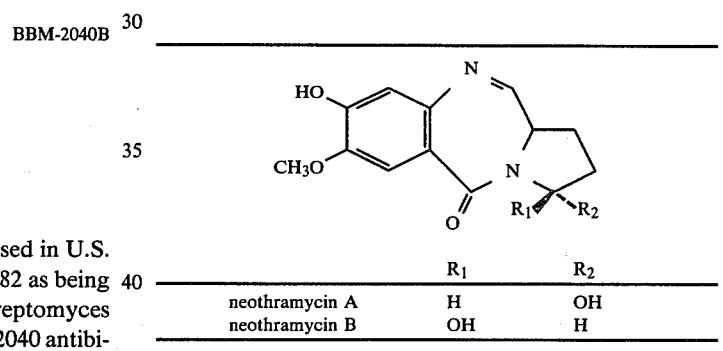

| | $R_1$ | $R_2$ |
|---|---|---|
| neothramycin A | H | OH |
| neothramycin B | OH | H |

The antibiotic BBM-2040B may be structurally differentiated from the neothramycins in the position of its hydroxyl group.

The antitumor antibiotic, tomaymycin, is disclosed in *J. Antibiotics* 25(8): 437–444 (1972) and *Chem. Pharm. Bull.* 19(11): 2289–2293 (1971) as being obtained by fermentation of *Streptomyces achromogenes* var. *tomaymyceticus*. Tomaymycin, which has the structure

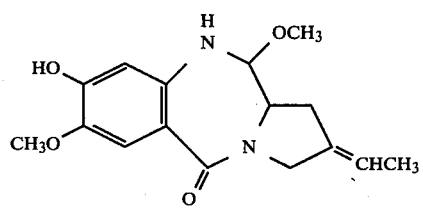

may be differentiated from BBM-2040A by the presence of the ethylidene group at the C-2 position.

The antitumor antibiotic, pretomaymycin, is disclosed in *J. Antibiotics* 25: 437 (1972) as having the structure

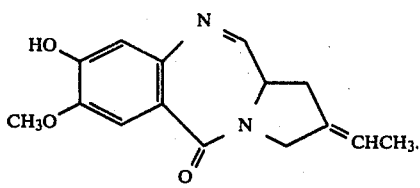

Pretomaymycin may be differentiated from BBM-2040B by the ethylidene group at the C-2 position.

The antitumor antibiotic, oxotomaymycin, having the formula

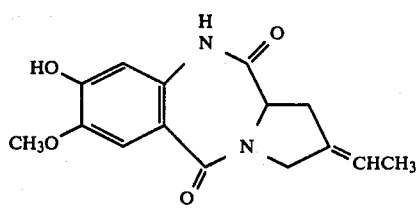

is disclosed in Chem. Pharm. Bull. 19: 2289 (1971). Oxotomaymycin differs from the BBM-2040 antibiotics in the presence of the 2-ethylidene group and the presence of the carbonyl group at C-11.

Among the members of the anthramycin group of antitumor antibiotics are anthramycin having the formula

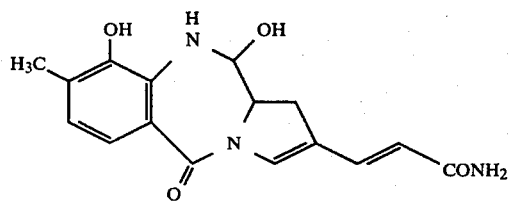

which is disclosed in J. Am. Chem. Soc. 87: 5791 (1965), mazethramycin having the formula

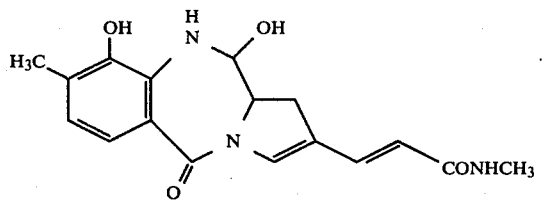

which is disclosed in J. Antibiotics 33(6): 665–667 (1980) and sibiromycin of the formula

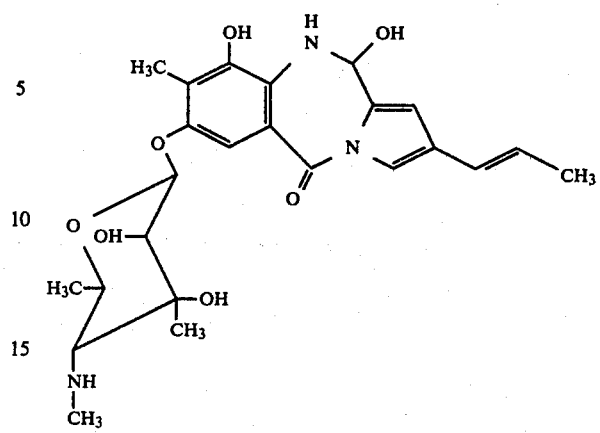

which is disclosed in J. Antibiotics 27(11): 866–873 (1974) and J. Antibiotics 25(11): 668–673 (1972).

An extensive comparison of anthramycin, tomaymycin and sibiromycin is found in J. Antibiotics 30(5): 349–370 (1977).

Procedures for total synthesis of anthramycin are disclosed in J. Am. Chem. Soc. 90: 5641–5643 (1968) and in J. Chem. Soc., Chem. Commun., 741–742 (1982).

Chem. Pharm. Bull 19: 2289–2293 (1971) discloses the reaction steps

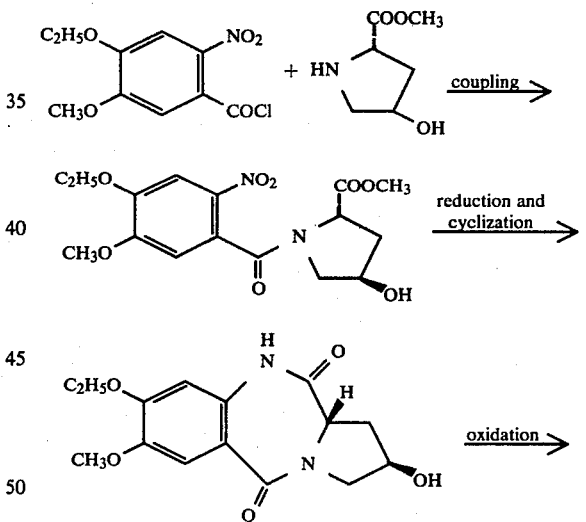

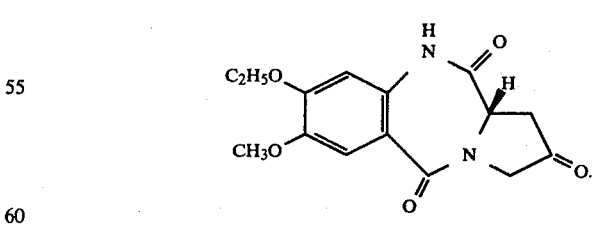

The above steps are substantially the same as steps (1), (2), (3) and (5) of the present process except that an ethyl group is used to protect the C-8 hydroxyl group. Such a protecting group is not readily removable and the resulting process, therefore, is not suitable for use in preparing the BBM-2040 antibiotics. This reference makes no suggestion of further converting the amide product to a carbinolamine product such as BBM-2040A.

SUMMARY OF THE INVENTION

The present invention provides a new method for the chemical synthesis of the pyrrolobenzodiazepine antibiotics, BBM-2040A and B, from readily available starting materials. The method provides a total synthesis alternative to the previously employed microbiological process for production of these useful antitumor antibiotics.

As mentioned above the BBM-2040 antibiotic has been isolated in two different forms depending on the isolation procedure employed. When methanol is employed as a solvent in the isolation procedure, the product is recovered in the methanol-adduct form (BBM-2040A), but in the absence of methanol, the desmethanol form (BBM-2040B) is obtained. By treating BBM-2040A with pyridine, it may be easily converted to the BBM-2040B form. Therefore, although the total synthesis of the present invention initially produces BBM-2040A, the invention encompasses production of both BBM-2040A and B since the A form may be easily converted to the B form by the additional step of treatment with pyridine.

The process of the present invention comprises the steps of (1) coupling a (lower)alkyl ester of trans-4-hydroxy-L-proline in an inert solvent with an acylating derivative of an acid of the formula

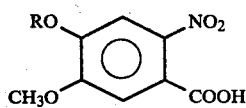

wherein R is a conventional phenolic hydroxyl protecting group to produce an intermediate of the formula

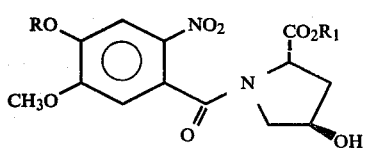

wherein $R_1$ is (lower)alkyl and R is as defined above;

(2) selectively reducing the nitro group of intermediate III to produce an intermediate of the formula

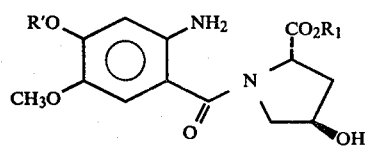

wherein R' is hydrogen or a conventional phenolic hydroxyl protecting group and $R_1$ is as defined above;

(3) cyclizing intermediate IV by heating in an inert solvent or by treatment with aqueous acid to produce an intermediate of the formula

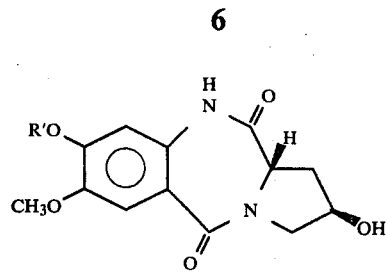

wherein R' is as defined above;

(4) in the case where R' in intermediate V is hydrogen, converting intermediate V to the corresponding intermediate of the formula

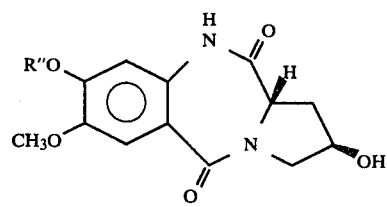

wherein R'' is a conventional phenolic hydroxyl protecting group;

(5) oxidizing the C-2 hydroxyl group of intermediate V or Va having the C-8 hydroxyl group protected with a conventional phenolic hydroxyl protecting group so as to produce an intermediate of the formula

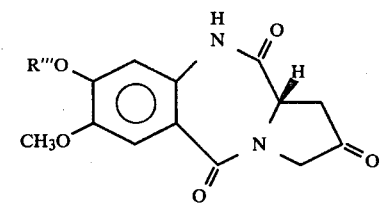

wherein R''' is R' or R'';

(6) selectively reducing the C-2 keto group of intermediate VI to produce the C-2 α-hydroxy isomer of the formula

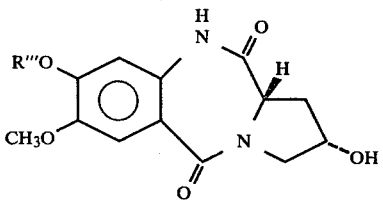

wherein R''' is as defined above;

(7) converting intermediate VII to the corresponding intermediate of the formula

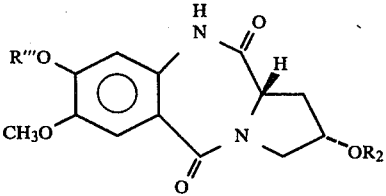

wherein R₂ is a conventional hydroxyl protecting group and R''' is as defined above;

(8) reacting amide intermediate VIII with phosphorous pentasulfide or 2,4-bis(4-methoxyphenyl)-1,3-dithia-2,4-diphosphetane-2,4-disulfide in an inert organic solvent to produce the thioamide intermediate of the formula

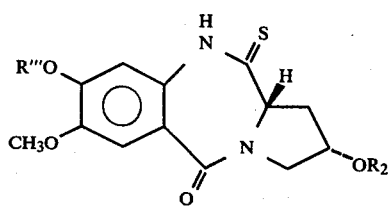   IX wherein R₂ and R''' are as defined above;

(9) reacting intermediate IX with a (lower)alkyl halide or (lower)alkoxonium salt in an inert organic solvent and in the presence of base to produce the thioiminoether intermediate of the formula

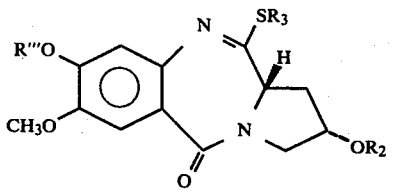   X wherein R₃ is (lower)alkyl and R₂ and R''' are as defined above;

(10) optionally removing the C-2 and C-8 hydroxyl protecting groups of intermediate X to form an intermediate of the formula

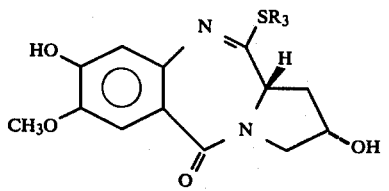   XI wherein R₃ is as defined above;

(11) selectively reducing the thioiminoether moiety of intermediate XI or intermediate X in an inert solvent to produce a thiocarbinolamine intermediate of the formula

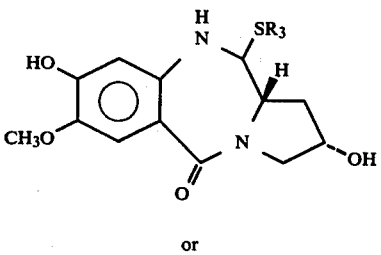   XII or

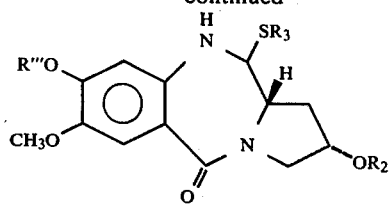   XII' wherein R₃, R''' and R₂ are as defined above; and

(12) reacting intermediate XII or XII' with a mercuric salt in methanol to form the carbinolamine product of the formula

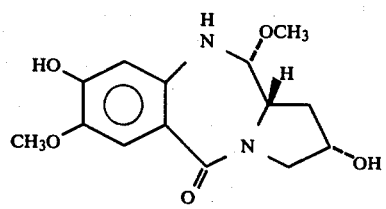   I or

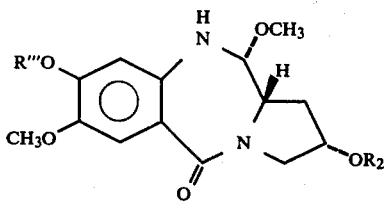   I' wherein R₂ and R''' are as defined above; and, when the product obtained is compound I', removing the hydroxyl protecting groups R₂ and R''' from intermediate I' so as to for the desired deprotected product I; and, if desired, treating said antibiotic with pyridine to form the corresponding desmethanol form of the antibiotic having the formula

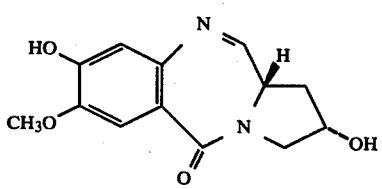   BBM-2040B

A preferred embodiment comprises reaction steps (8) through (12) since these steps provide a novel method of transforming an amide functional group in pyrrolo[1,4]benzodiazepine compounds to a carbinolamine functional group.

In another aspect the present invention provides the novel intermediates of formulae IX, X and XI and procedures for their synthesis. Preferred process embodiments comprise reaction step (8) of the above-described total synthesis for preparation of intermediate IX, step (9) for preparation of intermediate X and step (10) for preparation of intermediate XI.

DESCRIPTION OF THE DRAWINGS

FIG. 6 shows the ultraviolet absorption spectrum of BBM-2040B in acetonitrile, 0.1 N HCl-acetonitrile (1:9 v/v) and 0.1 N NaOH-acetonitrile (1:9 v/v).

DETAILED DESCRIPTION

Figure 1:
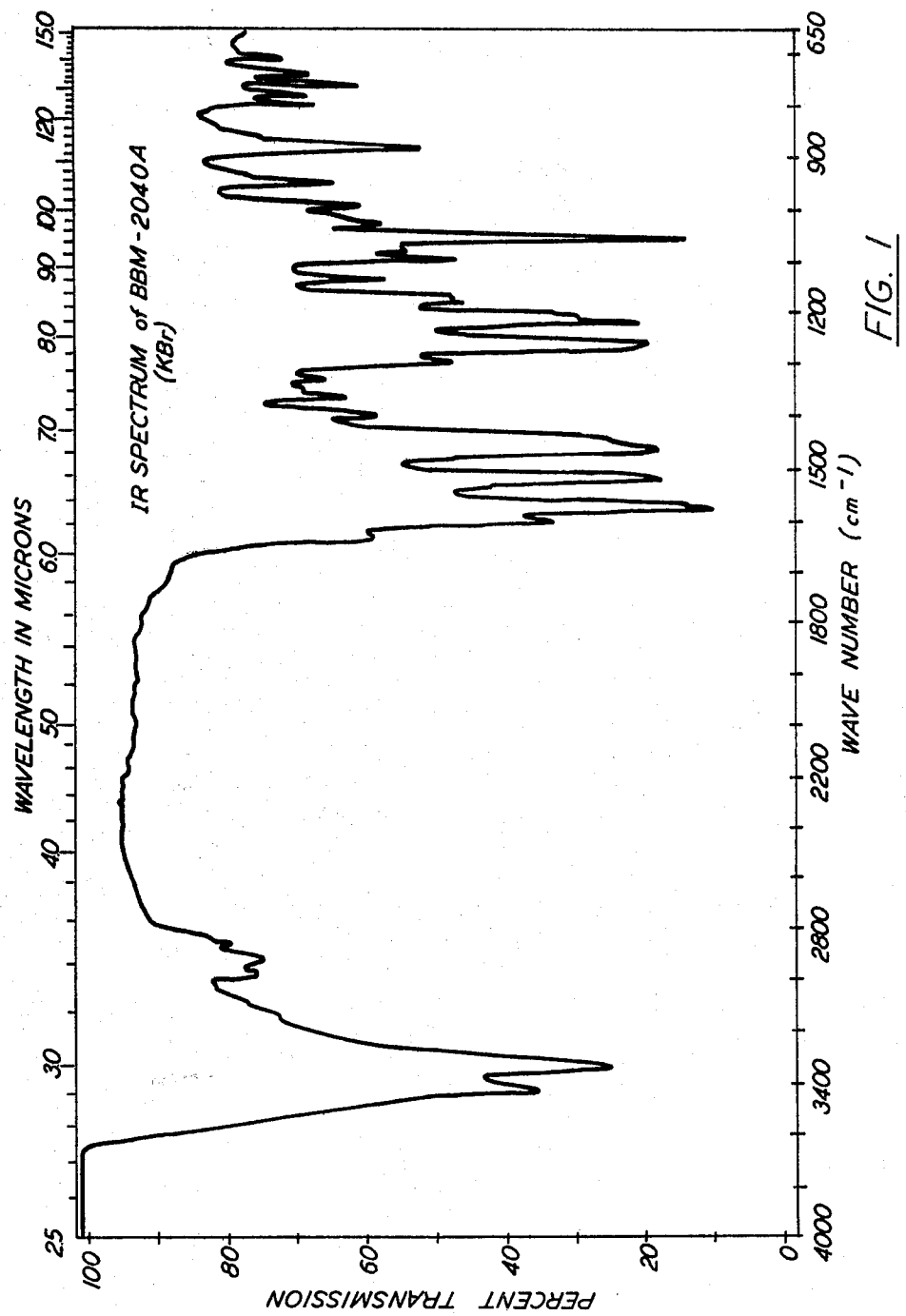
FIG. 1 shows the infrared absorption spectrum of BBM-2040A (KBr pellet).
Figure 2:
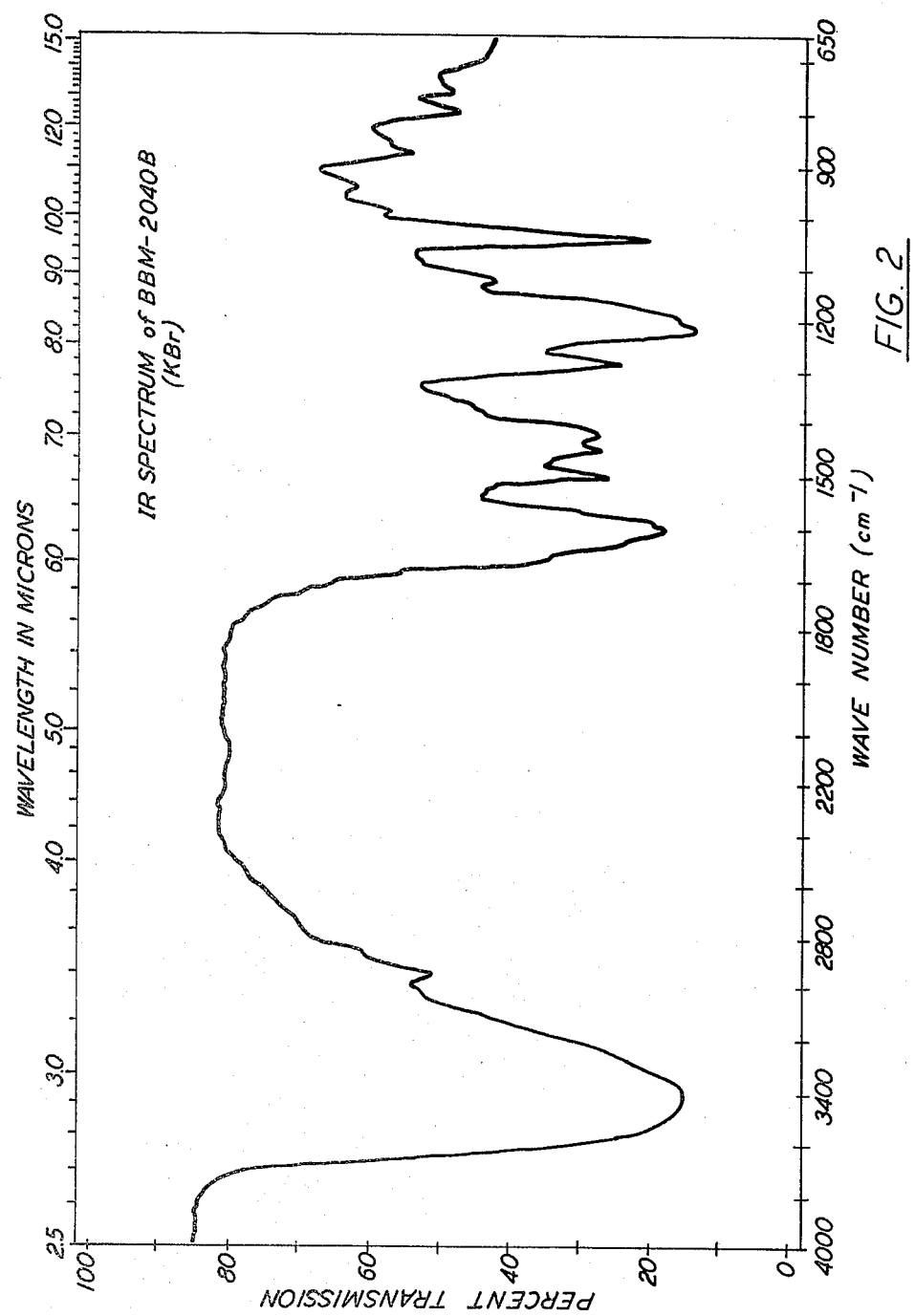
FIG. 2 shows the infrared absorption spectrum of BBM-2040B (KBr pellet).

To elaborate on the above-described process, step (1) involves an amide bond coupling reaction between a (lower)alkyl ester of trans-4-hydroxy-L-proline and an acylating derivative of an acid of the formula

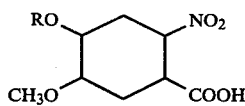

II wherein R represents a conventional phenolic hydroxyl protecting group.

The (lower)alkyl ester of trans-4-hydroxy-L-proline may be any $C_1$–$C_6$ alkyl ester. Such ester may be prepared from trans-4-hydroxy-L-proline by standard esterification procedures. For example, the methyl ester may be prepared by treatment of the amino acid with methanolic HCl.

The hydroxyl-protected benzoic acid II may be prepared according to known methods. For example, acid III where the hydroxyl protecting group is p-nitrobenzyl may be prepared from vanillic acid as described in *J. Antibiotics* 30(4): 341–342 (1977). In a slight variation of the published procedure, the same acid may be prepared from vanillic acid by first reacting with p-nitrobenzyl bromide to protect the phenolic hydroxyl group and then nitrating with concentrated nitric acid, acetyl nitrate or nitronium tetrafluoroborate at −78° to 0° C., preferably −50° C. to −60° C. Other hydroxyl-protected acids may be prepared in a similar way. The protecting group R may be any conventional hydroxyl protecting group which is stable to the nitration and coupling conditions employed. Thus, for example, it may be an ether such as p-nitrobenzyl or o-nitrobenzyl or an ester such as acetyl, trifluoroacetyl, benzoyl or p-toluenesulfonyl. Examples of other suitable phenolic hydroxyl protecting groups and methods for their introduction and removal are disclosed, for example, in Chapter 3 of *Protective Groups in Organic Chemistry*, T. W. Greene, Ed., Wiley-Interscience, New York, 1981.

To carry out the coupling of the amino acid ester and acid III, the acid must first be activated by one of the conventional acylation procedures used in peptide synthesis. For example, the acid may be converted to an acylating derivative such as an acid halide (particularly the acid chloride), a mixed acid anhydride (such as the acid anhydride formed with pivalic acid or a haloformate such as ethyl or isobutyl chloroformate) or an activated ester. The acylation may also be effected by use of the free acid III in the presence of a condensing agent such as dicyclohexylcarbodiimide, carbonyldiimidazole, N-ethoxy carbonyl-2-ethoxy-1,2-dihydroquinoline (EEDQ) or an isoxazolium salt. As used herein and in the claims, the term "acylating derivative" of the acid of formula III includes the free acid itself in the presence of a condensing agent such as described above. The preferred acylating derivative is the acid chloride which may be formed, for example, by reaction of the free acid with thionyl chloride or phosphorous pentachloride. Other suitable acylating derivatives and acylation coupling procedures are disclosed, for example, in *The Peptides*, E. Schroder and K. Lubke, Ed., Academic Press, New York, Vol. 1, p. 77 and following pages.

The particular process conditions, temperature, solvent, reaction time, etc. selected for the acylation coupling reaction are determined by the nature of the acylation method used and are known to those skilled in the art. Generally, it is useful to carry out the coupling in the presence of an acid acceptor, e.g. an organic tertiary amine such as triethylamine. An inert aqueous or non-aqueous solvent is employed. Examples of suitable non-aqueous organic solvents include dioxane, halogenated hydrocarbons (e.g. methylene chloride, chloroform), tetrahydrofuran, acetonitrile and the like.

Following the coupling step (1) to produce intermediate III, the nitro group of intermediate III is reduced to an amino group by either catalytic hydrogenation using a noble metal catalyst or by chemical reduction. For catalytic hydrogenation, catalysts such as Pd-C, $PtO_2$, Rh-C and Raney nickel can be utilized with the solvent being (lower) alcohols (i.e. $C_1$–$C_6$ alcohols), ethyl acetate, acetic acid, or the like. The hydrogen pressure can be between 1 and 50 psi, and the temperature can be between 0° C. and 50° C. For chemical reduction iron or zinc with acid, sodium sulfide or sodium dithionite can be used with the solvent being, for example, (lower) alcohols, aqueous tetrahydrofuran or aqueous dioxane.

Step (3) involves cyclization of the resultant amino intermediate IV to form lactam intermediate V. This can be effected by either heating IV in an inert organic solvent such as benzene, toluene or chlorobenzene at ∼50° C. to 150° C. or by treating IV with aqueous acid. The former type of cyclization has been reported in *Chem. Pharm. Bull.* 19: 2289–2293 (1971) and the latter in *J. Am. Chem. Soc.* 90:5641 (1968).

During the nitro group reduction step (2), the phenolic hydroxyl protecting group may be cleaved off to generate the free hydroxyl group (e.g. groups such as p-nitrobenzyl and o-nitrobenzyl are cleaved by catalytic hydrogenation). In such cases, it is necessary to re-protect the 8-OH group with a conventional phenolic hydroxyl protecting group such as acetyl, trifluoroacetyl, benzoyl, p-nitrobenzoyl, p-methoxybenzoyl or vinyloxycarbonyl which can be removed by mild base or trimethylsilyl, t-butyldimethylsilyl or diphenylmethylsilyl which can be removed with fluoride ion. Conveniently, the C-8 hydroxy group is selectively acylated by a conventional acylating reagent such as 1∼1.5 equivalent of acid chloride or acid anhydride and 1∼1.5 equivalent of base. For the base, pyridine, triethylamine and sodium hydride may be used. The preferred reagent system is benzoyl chloride (1.1 equivalent) as an acylating agent, NaH (1.1 equivalent) as the base, and dimethylformamide as the solvent. Another preferred protecting group for the C-8 hydroxy group is a (lower)organosilyl ether (the term "(lower)" used herein and in the claims refers to $C_1$–$C_6$ carbons). For silylation the preferred base is imidazole or triethylamine and dimethylformamide is the preferred solvent. Both acylation and silylation can be carried out at ~0° to room temperature. The phenolic hydroxyl protecting group is selected so as to withstand the reaction conditions of steps (5) through (9). Certain phenolic hydroxyl protecting groups such as acyl are not cleaved by reduction step (2) and, in such cases, intermediate V may be directly oxidized according to step (5).

In step (5) the intermediate V (if the phenolic hydroxyl protecting group has not been removed) or intermediate Va is oxidized so as to produce intermediate VI having a 2-keto group. Oxidation of the C-2 hydroxy group can be carried out according to well-known procedures using such oxidizing agents as Jones reagent, pyridinium chromate, dimethylsulfoxide-trifluoroacetic anhydride or dimethylsulfide-N-chlorosuccinimide. The reaction temperature may be between about −30° C. to +30° C. depending on the reagent used. Inert organic solvents such as acetone or halogenated hydrocarbons (e.g. methylene chloride) are employed.

In step (6) the 2-keto group of intermediate VI is selectively reduced using a metal hydride reducing agent under standard conditions. The metal hydride may be sodium borohydride, sodium cyanoborohydride, potassium tri-sec-butylborohydride, lithium tri-sec-butylborohydride and the like. The solvent may be, for example, a (lower)alcohol, dioxane or tetrahydrofuran. The reaction temperature may be between about 0° C. and 50° C. and is preferably room temperature. One to one and a half equivalents of reducing agent should preferably be used. The C-2 β-hydroxy isomer which may form during the reduction as a by-product may be removed chromatographically.

In step (7) the C-2 hydroxy group of the desired C-2 α-hydroxy isomer VII is protected by a conventional hydroxy protecting group removable under neutral or slightly basic conditions. Preferred protecting groups are acyl or organosilyl groups such as described for step (5). A large excess of acylating or silylating agent should be avoided since it may acylate or silylate the N-10 amide group. A most preferred protecting group is acetyl which may be introduced by acylation of alcohol VII with acetic anhydride. Other suitable protecting groups and methods for their introduction and removal are described in the literature, e.g. *Protective Groups in Organic Chemistry*, T. W. Greene, Ed., Wiley-Interscience, New York, 1981, Chapter 2.

The conversion of an amide functional group in a pyrrolo[1,4]benzodiazepine compound such as intermediate VIII to a carbinolamine group (such as in BBM-2040A) has never been reported in the literature. Accordingly, the remaining steps of the overall process, i.e. steps (8) through preparation of end-products BBM-2040A and B, constitute a preferred embodiment of the present invention.

Step (8) involves thiation of amide intermediate VIII to form thioamide intermediate IX. Thiation is carried out by reacting VIII in an inert organic solvent such as benzene, toluene, dioxane, and the like, with phosphorous pentasulfide or 2,4-bis(4-methoxyphenyl)-1,3-dithia-2,4-diphosphetane-2,4-disulfide (Lawesson's reagent). The molar ratio of the thiation reagent to amide VIII should be about 0.5~1.0 and preferably 0.5. The reaction temperature may be between about 50° C. to 150° C. The most preferred thiation reagent is Lawesson's reagent.

In step (9) the thioamide intermediate IX is alkylated to form thioiminoether intermediate X with a (lower)alkyl halide or (lower)alkoxonium salt in an inert organic solvent (e.g. tetrahydrofuran, methylene chloride, etc.). The preferred reagent-solvent system is methyl iodide (1~5 equivalents) in tetrahydrofuran or triethyloxonium tetrafluoroborate (1~1.5 equivalents) in methylene chloride. The alkylation reaction is typically carried out at about 0° C. to room temperature in the presence of an inorganic base (5-10 equivalents) such as $K_2CO_3$ or $NaHCO_3$.

After formation of intermediate X the C-2 and C-8 hydroxyl protecting groups may be cleaved by standard procedures. For example, if the protecting groups are both acyl groups, they may be cleaved with mild base such as methanolic $K_2CO_3$ or dilute aqueous NaOH solution. Similarly, if the protecting groups are organosilyl groups, they may be cleaved with a fluoride salt such as tetra-n-butylammonium fluoride. Since the thioiminoether intermediate is relatively labile, the deprotection reactions should be carried out below room temperature, preferably at about 0° C. If intermediate X contains both an acyl group and an organosilyl group, the protecting groups may be removed in a stepwise fashion using the reagents mentioned above.

Instead of removing the hydroxyl protecting groups at this stage of the overall process, one can proceed directly to reduction step (11) and subsequent steps and carry out the deprotection step after either of steps (11) or (12). Since, however, (12) is conveniently carried out without isolating intermediate XII or XII', i.e. steps (11) and (12) are done in a "one pot" reaction, it is most convenient to carry out deprotection either prior to reduction step (11) or after formation of carbinolamine I in step (12).

In step (11) the hydroxyl-protected intermediate X or de-protected intermediate XI is selectively reduced in an inert solvent to the corresponding thiocarbinolamine intermediate XII' or XII. This reduction step is preferably carried out by reaction with about one to twenty equivalents of aluminum amalgam in an aqueous ether such as diethyl ether, tetrahydrofuran or dioxane. The reaction can be carried out at from about −5° C. to room temperature, the preferred temperature being about 0° C. The reduction may also be carried out electrochemically using a $PbO_2$ electrode on a two-phase mixture of 10% aqueous $HClO_4$ solution and a halohydrocarbon (e.g. $CH_2Cl_2$, $CHCl_3$, and the like). Electrolytic reduction is done at about 0°-50° C. under a current density of 10-20 $mA/cm^2$.

After formation of the thiocarbinolamine intermediate XII' or XII, the alkylthio group of the intermediate is replaced with a methoxy group by treatment of the reduction mixture with about 0.5 to 1 equivalent of a mercuric salt (e.g. $HgCl_2$, $HgSO_4$, $Hg(CH_3COO)_2$, $HgBr_2$, etc.) in methanol. The exchange reaction (12) is carried out between about −10° C. and +30° C., preferably at about 0° C.

At the conclusion of step (12), the product is deprotected as in step (10) if hydroxyl protecting groups are still present.

The process of the present invention produces the methanol-adduct form of antibiotic BBM-2040 directly. If the desmethanol form is desired, however, an additional step may be performed in which the BBM-2040A antibiotic is dissolved in pyridine for a period of approximately three hours. Treatment with pyridine is found to convert substantially all of the methanol-adduct form to the desmethanol form.

The BBM-2040A and B antibiotics produced according to the present invention have the following physical properties:

Physico-Chemical Properties

BBM-2040A and BBM-2040B are readily soluble in methanol ethanol, n-butanol and pyridine, slightly soluble in ethyl acetate, acetone and water and practically insoluble in benzene, chloroform and n-hexane. Both forms of the antibiotic give positive reactions with ferric chloride, Rydon-Smith and ninhydrin (weak brownish pink) reagents, but are negative to Sakaguchi, Ehrlich and anthrone reactions. Molecular formulae of $C_{14}H_{18}N_2O_5$ and $C_{13}H_{14}N_2O_4$ were assigned to BBM-2040A and B, respectively, based on the $^{13}$C-NMR and mass spectral data and microanalysis. Physico-chemical properties of BBM-2040A and B are summarized in Tables 1, 2 and 3. The IR spectra of BBM-2040A and B (in KBr pellet) are shown in FIG.'s 1 and 2.

TABLE 1
Physico-chemical properties of BBM-2040A and B

|  | BBM-2040A | BBM-2040B |
|---|---|---|
| Nature | Colorless needles | White amorphous powder |
| M.p. | 161–163° C. (dec.) | 134–136° C. (dec.) |
| $[\alpha]_D^{26}$ (c 0.11, pyridine) | +350° | +552° |
| Molecular formula | $C_{14}H_{18}N_2O_5$ | $C_{13}H_{14}N_2O_4$ |
| Microanalysis | Calc'd    Found | Calc'd    Found |
| C % | 57.13    56.85 | 59.54 |
| H % | 6.16    6.16 | 5.38 |
| N % | 9.52    9.33 | 10.68 |
| Mass spectrum m/z | 294($M^+$), 262, 242, 219, 178, 150, 122, 86, etc. | 262($M^+$), 242, 150, 122, 86, etc. |

UV spectrum: $\lambda_{max}$ in nm ($\epsilon$)

|  | in CH$_3$CN | in N/10HCl.90% CH$_3$CN | in N/10NaOH.90% CH$_3$CN |
|---|---|---|---|
| BBM-2040A | 223 (23,800) | 221 (19,200) | 230 (18,000) |
|  | 233$^{sh}$ (21,600) | 260$^{sh}$ (7,900) | 254$^{sh}$ (15,100) |
|  | 256$^{sh}$ (6,800) | 290$^{sh}$ (2,800) | 287 (14,000) |
|  | 323 (3,900) | 320 (1,200) | 317 (10,100) |
| BBM-2040B | 225 (19,400) | 222 (16,600) | 234 (17,900) |
|  | 234$^{sh}$ (17,800) | 260$^{sh}$ (7,100) | 253 (17,300) |
|  | 258$^{sh}$ (7,400) | 290$^{sh}$ (2,900) | 288 (12,600) |
|  | 312 (2,900) | 323 (1,900) | 318 (11,300) |

TABLE 2
PMR (360 MHz) of BBM-2040A (in pyridine-d$_5$)

| Chemical shift δ (ppm) | Proton | Coupling multiplicity (J:Hz) | Assignment |
|---|---|---|---|
| 2.39 | 1H | m | H$_{1A}$ |
| 2.57 | 1H | m | H$_{1B}$ |
| 3.30 | 3H | s | C$_{11}$—OCH$_3$ |
| 3.75 | 3H | s | C$_7$—OCH$_3$ |
| 4.08 | 1H | t (8.1) | H$_{11a}$ |
| 4.14 | 1H | dd (12.0 & 5.8) | H$_{3A}$ |
| 4.48 | 1H | dd (12.0 & 6.0) | H$_{3B}$ |
| 4.53 | 1H | m | H$_2$ |
| 4.77 | 1H | d (J = 6.4) | H$_{11}$ |
| 6.34 | 1H | d (J = 7.4) | C$_2$—OH |
| 6.88 | 1H | s | H$_9$ |
| 7.94 | 1H | d (J = 6.4) | N$_{10}$—H |
| 8.17 | 1H | s | H$_6$ |
| 11.68 | 1H | s | C$_8$—OH |

TABLE 3
$^{13}$C-NMR of BBM-2040A (in pyridine-d$_5$)

| Carbon | Chemical shift (δ: ppm) | Multiplicity on off-resonance |
|---|---|---|
| 1 | 25.0 | t |
| 2 | 43.4 | d |
| 3 | 41.9 | t |
| 5 | 151.7 | s |
| 5a | 126.8* | s |
| 6 | 90.0 | d |
| 7 | 137.5 | s |
| 8 | 150.1 | s |
| 9 | 101.6 | d |
| 9a | 125.4* | s |
| 11 | 73.4 | d |
| 11a | 53.3 | d |
| 7-OCH$_3$ | 41.4** | q |
| 11-OCH$_3$ | 38.9** | q |

*,**Assignments may be interchangeable.

Figure 3:
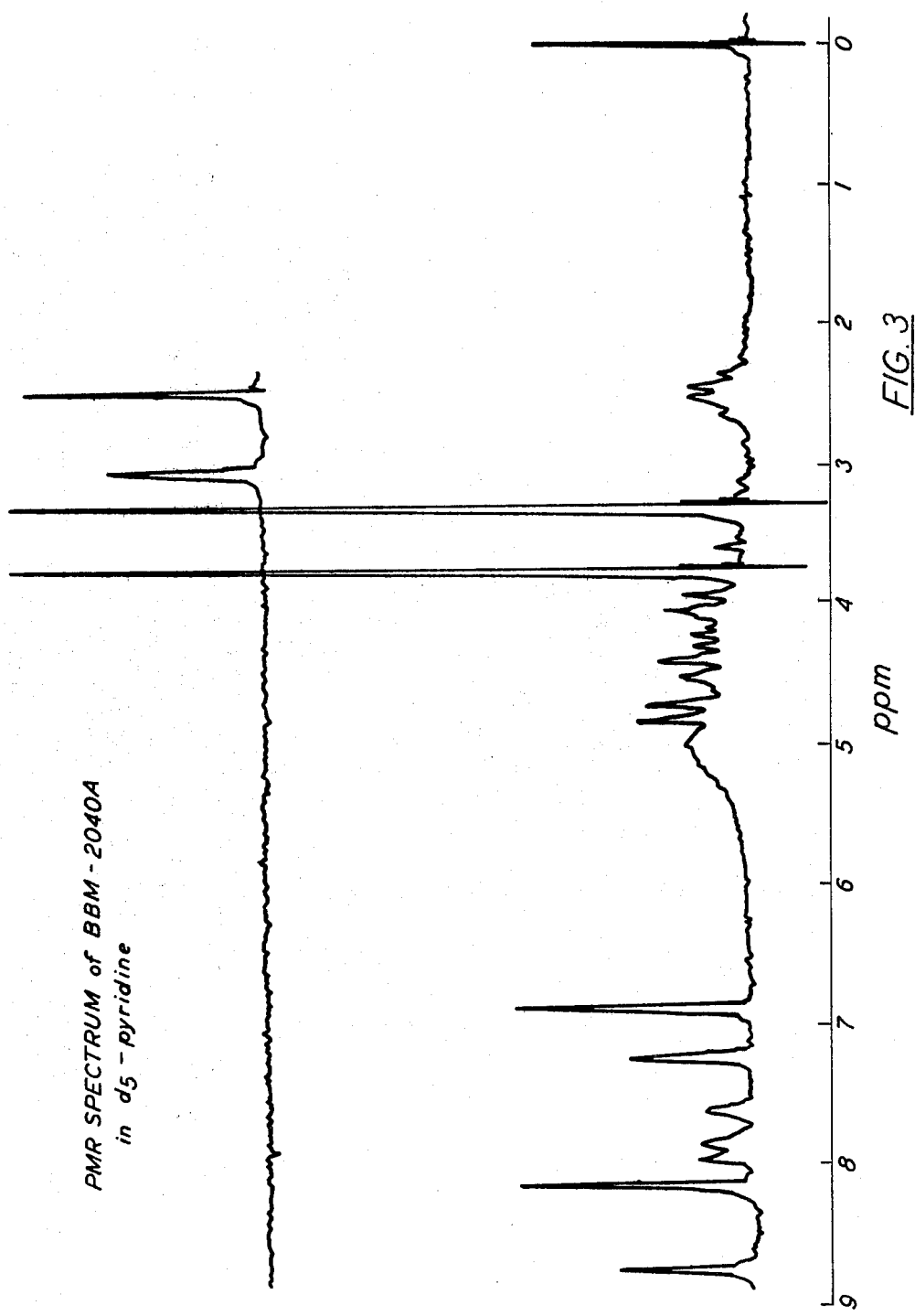
FIG. 3 shows the PMR spectrum of BBM-2040A in pyridine-$d_5$ (60 MHz).
Figure 4:
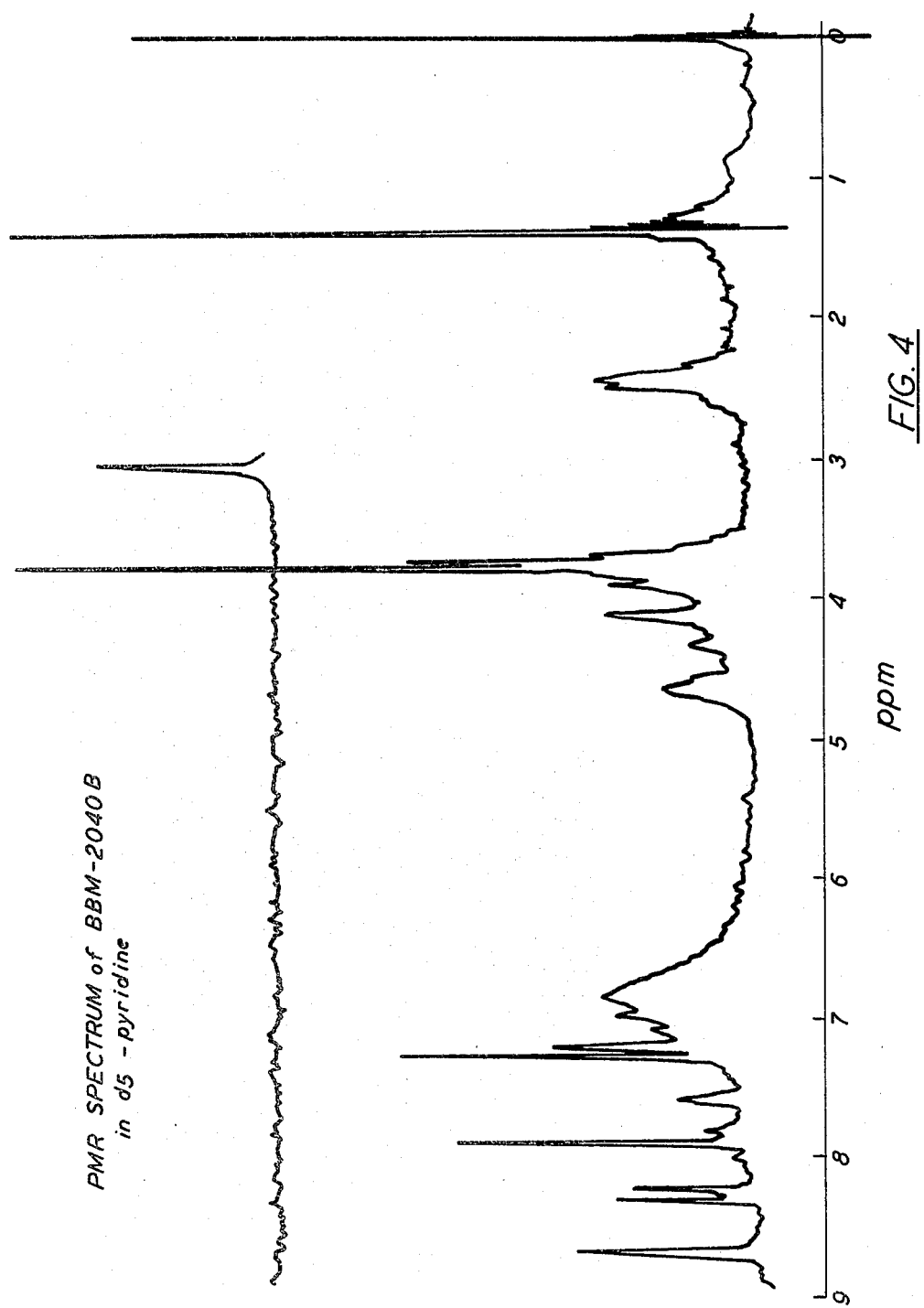
FIG. 4 shows the PMR spectrum of BBM-2040B in pyridine-$d_5$ (60 MHz).
Figure 5:
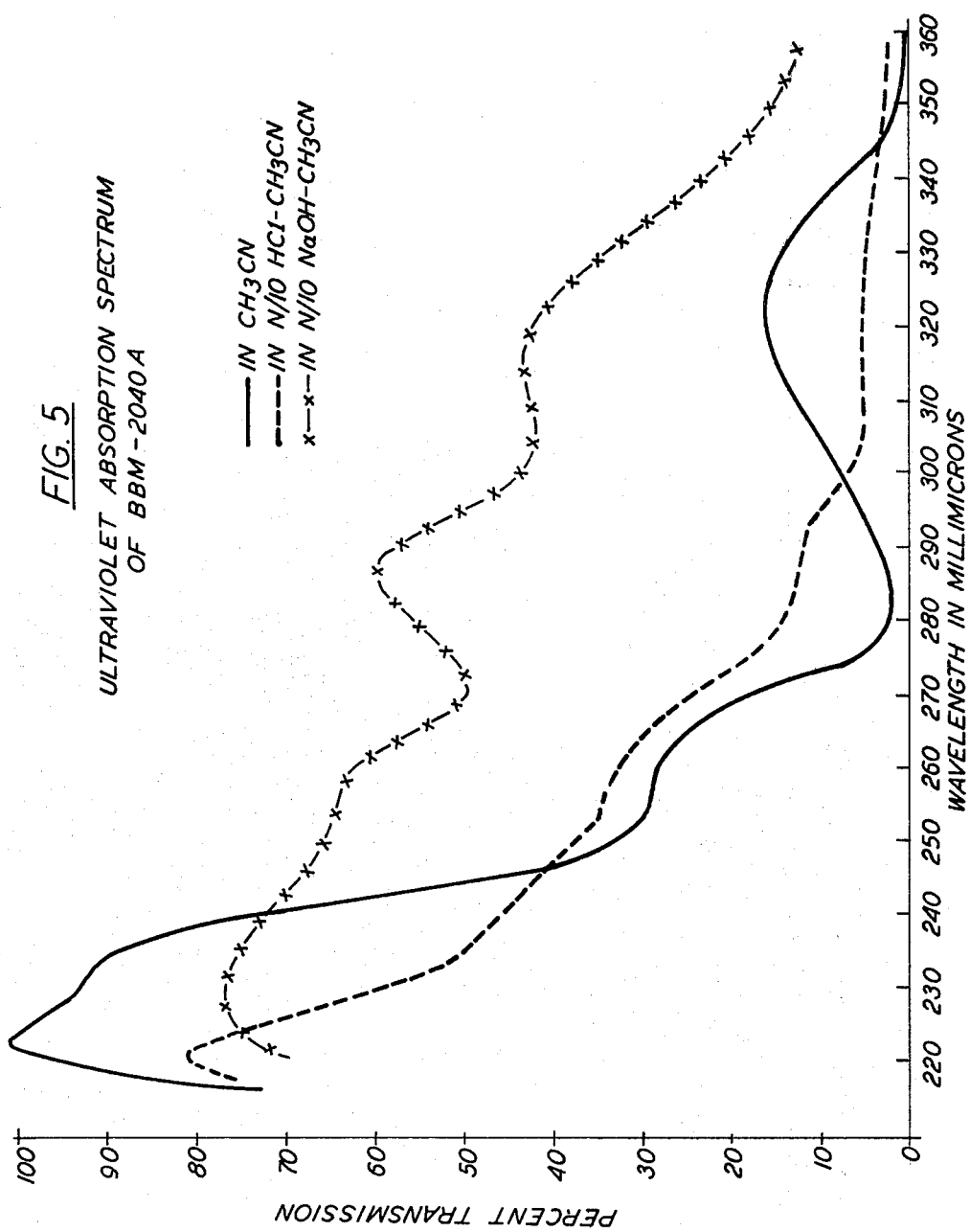
FIG. 5 shows the ultraviolet absorption spectrum of BBM-2040A in acetonitrile, 0.1 N HCl-acetonitrile (1:9 v/v) and 0.1 N NaOH-acetonitrile (1:9 v/v).

The PMR spectrum of BBM-2040A (FIG. 3, 60 MHz, pyridine-d$_5$) involves two OCH$_3$ groups (δ: 3.30 and 3.75 ppm), one high-field methylene group (δ: 2.1 ppm), five protons at around δ: 3.9–4.8 ppm and two aromatic protons (δ: 6.82 and 8.10 ppm), along with one NH (δ: 7.84 ppm) and two OH (δ: 6.2 and 11.50 ppm) signals. The PMR spectrum of BBM-2040B lacks the signals of higher-field OCH$_3$ and NH protons observed with BBM-2040A, while a double bond proton (δ: 8.24 ppm) is present in the spectrum of BBM-2040B. The physico-chemical properties of BBM-2040A and B described above are similar to those of neothramycin and tomaymycin, the 1,4-benzodiazepine group of antibiotics. However, the antibiotics are readily distinguished by their TLC behavior (Table 4) and PMR spectra. BBM-2040A and B cannot be differentiated by the three TLC systems examined.

TABLE 4
TLC of BBM-2040A and B and related antibiotics

| Solvent system | BBM-2040A | BBM-2040B | Neothramycin | Tomaymycin |
|---|---|---|---|---|
| Ethyl acetate-methanol (4:1) | 0.29 | 0.29 | 0.48 & 0.40 | 0.51 |
| Chloroform-methanol (5:1) | 0.24 | 0.24 | 0.42 & 0.32 | 0.52 |
| Ethyl acetate-acetonitrile (1:1) | 0.02 | 0.02 | 0.14 & 0.08 | 0.18 |

Biological Properties of BBM-2040A and B

As mentioned above, BBM-2040A and B inhibit the growth of various bacteria and mammalian tumors. A more detailed description of the biological properties of the antibiotics is provided below.

The minimum inhibitory concentration (MIC) of BBM-2040 was determined for a variety of gram-positive, gram-negative and acid-fast bacteria by the serial two-fold agar dilution method. Nutrient agar medium was used for gram-positive and gram-negative organisms and No. 1001 medium (3% glycerol, 0.3% sodium L-glutamate, 0.2% peptone, 0.31% Na$_2$HPO$_4$, 0.1% KH$_2$PO$_4$, 0.005% ammonium citrate, 0.001% MgSO$_4$ and 1.5% agar) for acid-fast organisms. As shown in Table 5, BBM-2040 A and B showed weak antibacterial activity against Streptococcus pyogenes, Micrococcus luteus, Micrococcus flavus and Mycobacterium strains. The antibacterial spectrum of BBM-2040 is similar to that of neothramycin. BBM-2040 does not induce prophage in lysogenic bacteria up to a concentration of 100 mcg/ml.

TABLE 5

Antibacterial activity of BBM-2040 A and B

| | MIC (mcg/ml) | | |
|---|---|---|---|
| Test organisms | BBM-2040 A | BBM-2040 B | Neothramycin |
| *Staphylococcus aureus* FDA 209P | >100 | >100 | >100 |
| *Staphylococcus aureus* Smith | >100 | >100 | >100 |
| *Streptococcus pyogenes* A20201 | 50 | 50 | 50 |
| *Streptococcus pyogenes* PCI 1001 | 50 | 100 | 100 |
| *Micrococcus flavus* D12 | 50 | 50 | 100 |
| *Bacillus subtilis* PCI 219 | >100 | >100 | 50 |
| *Mycobacterium smegmatis* 607 | 100 | 100 | >100 |
| *Mycobacterium phlei* D88 | 100 | 100 | >100 |
| *Escherichia coli* NIHJ | >100 | >100 | 50 |
| *Escherichia coli* Juhl | >100 | >100 | >100 |
| *Klebsiella pneumoniae* D-11 | >100 | >100 | 100 |
| *Proteus vulgaris* A9436 | >100 | >100 | 100 |
| *Pseudomonas aeruginosa* A9930 | >100 | >100 | >100 |

The antitumor activity of BBM-2040A and B was determined in mice (BDF$_1$ strain) against lymphocytic leukemia P388. Each mouse was inoculated intraperitoneally with 10$^6$ cells of tumor. Graded doses of test compounds were administered to mice intraperitoneally 24 hours after the tumor implantation. The treatments were given once daily for 9 days (qd 1→9 schedule). Neothramycin was comparatively tested as a reference compound. The results are shown in Table 6. BBM-2040A and neothramycin were similarly active in this experiment, while BBM-2040B was somewhat less active than BBM-2040A.

The acute toxicity of BBM-2040A and B was determined in mice (ddY strain) by single intraperitoneal administration, the LD$_{50}$ being 34 mg/kg and 57 mg/kg respectively. The intraperitoneal LD$_{50}$ of neothramycin has been reported to be 20–30 mg/kg.

TABLE 6

Antitumor activity against leukemia P388

| | T/C (%) in MST* Dose in mg/kg/day (ip) | | | | | |
|---|---|---|---|---|---|---|
| | 10 | 3 | 1 | 0.3 | 0.1 | 0.03 |
| BBM-2040 A | (152)** | (152) | (128) | 104 | 96 | |
| BBM-2040 B | (128) | (128) | 112 | 96 | 104 | |
| Neothramycin | — | (152) | (136) | 112 | 104 | 96 |

*ratio of median survival time of test and control animals
**circle indicates significant antitumor effect.

Antitumor activity of BBM-2040A was also demonstrated by a second experiment in which BBM-2040A was tested against P388 leukemia comparatively with neothramycin and the 2β-hydroxy epimer of BBM-2040A. In this experiment lymphatic leukemia P388 was implanted intraperitoneally into male BDF$_1$ mice at an inoculum size of 10$^6$ cells per mouse. Test compounds were dissolved in 0.9% saline containing 10% dimethylsulfoxide. Graded doses of test compounds were administered to mice intraperitoneally 24 hours after the tumor implantation, and the treatment was continued once daily for 9 days. Results of the experiment are shown below in Table 7. BBM-2040A and neothramycin were similarly active, while the 2β-hydroxy epimer of BBM-2040A was inactive at 1 mg/kg/day, the highest dose tested.

TABLE 7

Antitumor Activity against leukemia P388

| Material | Dose (mg/kg/day) | MST Days | Effect MST % T/C | Average weight change (g) | Survivors Day 5 | Survivors Day 22 |
|---|---|---|---|---|---|---|
| 2β-Hydroxy epimer of BBM-2040 A | 1 | 12.0 | 100 | +1.0 | 6/6 | 0/6 |
| | 0.3 | 11.0 | 92 | +1.8 | 6/6 | 0/6 |
| | 0.1 | 11.0 | 92 | +1.3 | 6/6 | 0/6 |
| | 0.03 | 10.5 | 88 | +1.0 | 6/6 | 0/6 |
| BBM-2040 A | 10 | 19.5 | 163 | −2.2 | 6/6 | 1/6 |
| | 3 | 17.0 | 142 | +0.5 | 6/6 | 0/6 |
| | 1 | 16.0 | 133 | +1.0 | 6/6 | 0/6 |
| | 0.3 | 14.0 | 117 | +1.3 | 6/6 | 0/6 |
| | 0.1 | 12.0 | 100 | +1.5 | 6/6 | 0/6 |
| Neothramycin | 3 | 17.5 | 146 | 0.0 | 6/6 | 0/6 |
| | 1 | 17.0 | 142 | +0.5 | 6/6 | 0/6 |
| | 0.3 | 14.5 | 121 | +0.8 | 6/6 | 0/6 |
| | 0.1 | 13.0 | 108 | +1.0 | 6/6 | 0/6 |
| Control | Saline | 12.0 | — | +1.3 | 12/12 | 0/12 |

Tumor inoculum: 10$^6$ ascites cells implanted i.p.
Host: ♂ BDF$_1$ mice
Treatment: QD 1→9, i.p.
Evaluation: MST = median survival time
Effect: % T/C = (MST treated/MST control) × 100
Criteria: % T/C ≧ 125 considered as significant antitumor activity As shown above BBM-2040 A and B possess antibacterial activity against various gram-positive and acid-fast bacteria and are thus useful in the therapeutic treatment of mammals and other animals for infectious diseases caused by such bacteria. Additionally, they may be utilized for other conventional applications of antibacterial agents such as disinfecting medical and dental equipment.

The marked antitumor activity shown against P388 leukemia in mice indicate that BBM-2040A and B are also therapeutically useful in inhibiting the growth of mammalian tumors.

The BBM-2040A and B compounds are preferably employed as pharmaceutical compositions, i.e. an effective anti-bacterial or tumor-inhibiting amount of BBM-2040A or B in combination with an inert pharmaceutically acceptable carrier or diluent. These compositions may be made up in any pharmaceutical form appropriate for parenteral administration.

Preparations for parenteral administration may include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred amounts of the BBM-2040 antibiotic used will vary according to the particular composition formulated, the mode of application and the particular situs, host and disease being treated. Many factors that modify the action of the drug will be taken into account by those skilled in the art, for example, age, body weight, sex, diet, time of administration, route of administration, rate of excretion, condition of the host, drug combinations, reaction sensitivities and severity of the disease. Administration can be carried out continuously or periodically within the maximum tolerated dose. Optimal application rates for a given set of conditions can be ascertained by those skilled in the art using conventional dosage administration tests in view of the above guidelines.

The following examples are not limiting but are intended to be illustrative of the present invention. Melting points reported below were determined on a Thomas-Hoover capillary apparatus and are uncorrected. NMR spectra were obtained on a Varian XL-100 or Bruker WM 360 spectrometer using tetramethylsilane as internal standard. IR spectra were obtained on a Beckman 4240 spectrophotometer. Mass spectra were recorded on DuPont DP-102 by direct introduction probe. Optical rotation measurements were taken on a Perkin-Elmer 241 MC polarimeter. High resolution mass spectra were obtained by Schrader Laboratories, Detroit, Michigan.

EXAMPLE 1

Preparation of 2(S),11(R),11a(S)-1,2,3,10,11,11a-Hexahydro-2,8-dihydro-7,11-dimethoxy-5H-pyrrolo[2,1c][1,4]benzodiazepin-5-one (BBM-2040A)

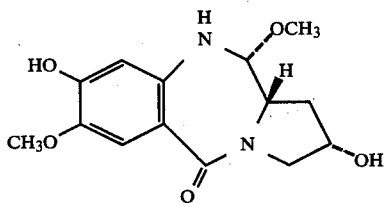

EXAMPLE 1

Preparation of BBM-2040A

A.

N-[5-methoxy-2-nitro-4-(4-nitrobenzyloxy)benzyl]-trans-4-hydroxy-L-proline methyl ester (4)

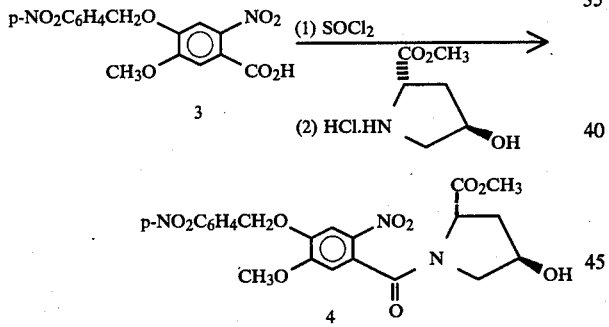

Acid 3 (*J. Antibiotics* 29:93–96, 1976) (5.25 g, 15 mmol) and thionyl chloride (2.86 g, 24 mmol) in 80 ml of tetrahydrofuran (THF) were refluxed for 2 hours. The solvent and excess reagent were removed under reduced pressure, and the residue was redissolved in 50 ml of THF. Separately, trans-4-hydroxy-L-proline methyl ester (2.725 g, 14 mmol) was dissolved in 50 ml of CH$_2$Cl$_2$ containing 3.39 g of triethylamine, and this solution was cooled to −20° C. The acid chloride solution prepared above was added dropwise to this solution. After 30 minutes of stirring at −20° C., the reaction mixture was diluted with CH$_2$Cl$_2$ and washed with 5% HCl solution and brine. Drying over Na$_2$SO$_4$ and removal of the solvent gave 7.20 g of an oil. This material was chromatographed on silica gel (3% CH$_3$OH—CH$_2$Cl$_2$) to give 6.00 g (84% yield) of 4 as foam: IR(KBr) 3430, 1744, 1635, 1522, 1431, 1346, 1280 cm$^{-1}$; NMR (CDCl$_3$, δ) 2.0–2.5 (m, 2H), 3.16 (bd, 1H, J=11 Hz), 3.56 (dd, 1H, J=11, 4 Hz), 3.85 (s, 3H), 4.02 (s, 3H), 4.46 (m, 1H), 4.86 (t, 1H, J=8 Hz), 5.32 (s, 2H), 6.92 (s, 1H), 7.68 (d, 2H, J=8 Hz), 7.76 (s, 1H), 8.26 (d, 1H, J=8 Hz).

Anal. Calc'd for C$_{21}$H$_{21}$N$_3$O$_{10}$: C, 53.05; H, 4.47; N, 8.84 Found: C, 52.72; H, 4.67; N, 8.50

B.

2(R),11a(S)-1,2,3,10,11,11a-Hexahydro-2,8-dihydroxy-7-methoxy-5H-pyrrolo[2,1-c]-1,4-benzodiazepin-5,11-dione (5)

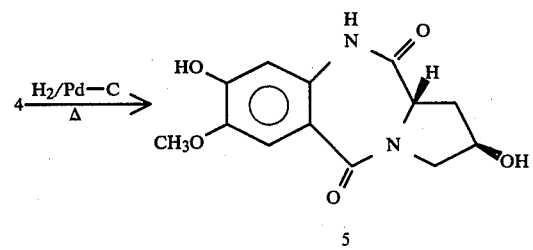

Nitro compound 4 (4.40 g, 9.26 mmol) in 120 ml of ethyl acetate and 40 ml of CH$_3$OH was hydrogenated at 20 psi of hydrogen in the presence of 1 g of 5% Pd on carbon. After 3 hours of shaking in a Parr apparatus, the mixture was filtered through CELITE and the solvent was evaporated under reduced pressure. The residue was dissolved in toluene and refluxed for 3 hours. The product, which precipitated out upon cooling, was collected by filtration (2.55 g, 99% yield): mp 260°–262° C. (CH$_3$OH); IR(KBr) 3465, 3340, 3250, 1680, 1630, 1612, 1523, 1493, 1435, 1280 cm$^{-1}$; NMR (pyridine-d$_5$, δ) 2.53 (m, 1H), 3.31 (dd, 1H, J=13, 6 Hz), 3.76 (s, 3H), 3.94 (dd, 1H, J=12, 4 Hz), 4.42 (dd, 1H, J=12, 3 Hz), 4.66 (dd, J=13, 6 Hz), 4.89 (m, 1H), 7.11 (s, 1H), 7.84 (s, 1H), 11.84 (s, 1H), 12.40 (bs, 1H); [α]$_D^{25}$ = +329° (C=0.251, CH$_3$OH); observed mass 278.0901 (calc'd for C$_{13}$H$_{14}$N$_2$O$_5$, 278.0901).

C.

2(R),11a(S)-1,2,3,10,11,11a-Hexahydro-8-benzoyloxy-2-hydroxy-7-methoxy-5H-pyrrolo[2,1-c][1,4]benzodiazepin-5,11-dione (6)

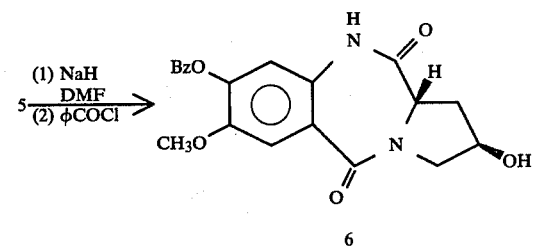

Bz = benzoyl

Dimethylformamide (DMF) (20 ml) was added to a mixture of NaH (262 mg, 11 mmol) and phenol intermediate 5 (2.78 g, 10 mmol), and the resulting solution was stirred at room temperature for 1 hour. Benzoyl chloride (1.55 g, 11 mmol) was added at −20° C. and stirring was continued for an additional 1 hour. DMF was then removed under reduced pressure and 10 ml of water was added to the residue. The precipitate which formed was collected by filtration and dissolved in 10% CH$_3$OH—CH$_2$Cl$_2$. Drying over Na$_2$SO$_4$ and removal of the solvent gave 3.82 g (100% yield) of benzoate intermediate 6: mp 258°–260° C.; IR(KBr) 3410, 1742, 1690, 1630, 1610, 1508, 1435, 1263, 1246, 1220 cm$^{-1}$;

NMR (CDCl$_3$—CD$_3$OD, δ) 2.13 (ddd, 1H, J=13, 8, 4 Hz), 2.89 (dt, 1H, J=13, 5 Hz), 3.66 (dd, 1H, J=13, 4 Hz), 4.56 (m, 1H), 6.96 (s, 1H), 7.41-7.80 (m, 4H), 8.22 (dd, 2H, J=8, 1 Hz).

Anal. Calc'd for C$_{20}$H$_{18}$N$_2$O$_4$.0.25H$_2$O: C, 62.09; H, 4.82; N, 7.24; Found: C, 61.90; H, 4.71; N, 7.60.

D.
11a(S)-1,2,3,10,11,11a-Hexahydro-8-benzoyloxy-7-methoxy-5H-pyrrolo[2,1-c][1,4]benzodiazepin-2,5,11-trione(7)

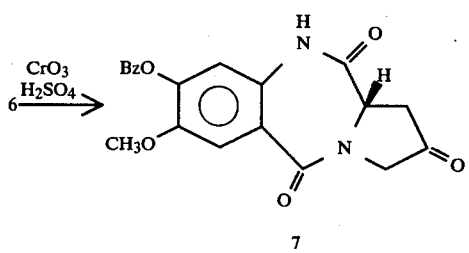

Alcohol intermediate 6 (3.82 g, 10 mmol) was dissolved in 150 ml of acetone and treated with 7 ml of Jones reagent at room temperature for 3.5 hours. After filtration through CELITE, the solvent was removed under reduced pressure. The residue was dissolved in CH$_2$Cl$_2$ and washed with brine. Drying over MgSO$_4$ and removal of the solvent gave 3.15 g (83% yield) of a slightly yellow solid 7. An analytical sample was prepared by recrystallization from CH$_2$Cl$_2$-ether: mp 224°-226° C.; IR(KBr) 3300, 1760, 1740, 1690, 1635, 1505, 1428, 1260, 1242 cm$^{-1}$; NMR (DMSO-d$_6$ δ), 2.89 (dd, 1H, J=20, 10 Hz), 3.26 (dd, 1H, J=20, 4 Hz), 3.87 (s, 3H), 3.91 (d, 1H, J=18 Hz), 4.20 (d, 1H, J=18 Hz), 4.71 (dd, 1H, J=10, 4 Hz), 7.12 (s, 1H), 7.53 (s, 1H), 7.56-7.90 (m, 3H), 8.16 (m, 2H); [α]$_D^{24}$=+388° (C=0.55, CH$_3$OH).

Anal. Calc'd for C$_{20}$H$_{16}$N$_2$O$_6$: C, 63.16; H, 4.24; N, 7.36; Found: C, 62.80; H, 3.96; N, 6.68.

E.
2(S),11a(S)-1,2,3,10,11,11a-Hexahydro-8-benzoyloxy-2-hydroxy-7-methoxy-5H-pyrrolo[2,1-c][1,4]benzodiazepin-5,11-dione (8)

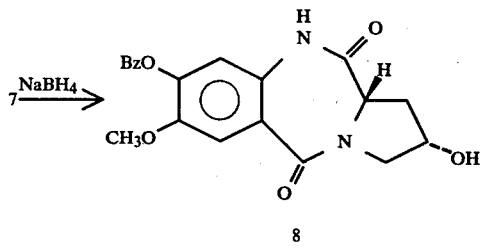

Ketone intermediate 7 (380 mg, 1 mmol) was dissolved in 16 ml of ethanol and 10 ml of CH$_2$Cl$_2$. NaBH$_4$ (11 mg, 0.3 mmol) was added at −20° C. and the resulting solution was stirred at this temperature for 30 minutes. After an addition of 10% HCl solution, the reaction mixture was diluted with CH$_2$Cl$_2$ and washed with brine. Drying over Na$_2$SO$_4$ and removal of the solvent gave a colorless oil which was a mixture of epimeric alcohols, 6 and 8 with the latter being predominant. They were separated by medium pressure liquid chromatography (MPLC) (silica gel, 5% CH$_3$OH—CH$_2$Cl$_2$) and the title compound (237 mg, 62% yield) was crystallized from CH$_2$Cl$_2$-ether: mp 250°-251° C.; IR(KBr) 3410, 1745, 1698, 1638, 1615, 1510, 1490, 1265, 1223 cm$^{-1}$; NMR (acetone-d$_6$, +DMSO-d$_6$, δ) 2.38 (ddd, 1H, J=14, 9, 5 Hz), 2.74 (bd, 1H, J=14 Hz), 3.54 (bd, 1H, J=12 Hz), 3.84 (dd, 1H, J=12, 4 Hz), 3.91 (s, 3H), 4.35 (dd, 1H, J=9, 4 Hz), 4.46 (m, 1H), 7.18 (s, 1H), 7.52-7.82 (m, 4H), 8.22 (dd, 1H, J=8, 2 Hz); [α]$_D^{25}$=+265° (C=0.32, CH$_3$OH).

Anal. Calc'd for C$_{20}$H$_{18}$N$_2$O$_6$: C, 62.84; H, 4.74; N, 7.33; Found: C, 62.54; H, 4.49; N, 7.18.

F.
2(S),11a(S)-1,2,3,10,11,11a-Hexahydro-2-acetoxy-8-benzoyloxy-7-methoxy-5H-pyrrolo-[2,1-c][1,4]benzodiazepin-5,11-dione (9)

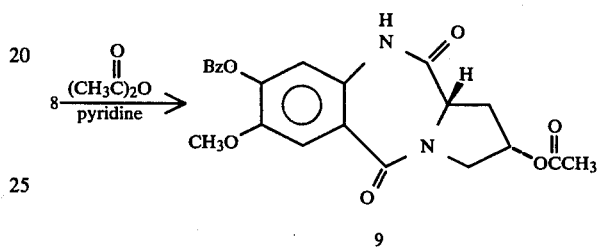

Alcohol intermediate 8 (203 mg, 0.53 mmol) was dissolved in 0.5 ml of pyridine and diluted with 5 ml of CH$_2$Cl$_2$. Acetic anhydride (0.1 ml, 1.05 mmol) was added and the resulting solution was stirred overnight at room temperature. Additional acetic anhydride (0.30 ml, 0.32 mmol) was added and stirring was continued at room temperature for 6 hours. The solvent and excess reagents were removed under reduced pressure. The residue was dissolved in CH$_2$Cl$_2$ and washed with 10% HCl solution. Drying over Na$_2$SO$_4$ and removal of the solvent gave a colorless glass. Chromatographic separation (silica gel, 1.5% CH$_3$OH—CH$_2$Cl$_2$) and recrystallization (CH$_2$Cl$_2$-ether) gave 121 mg of the title compound: mp 229°-230.5° C.; IR(KBr) 3460, 3250, 1740, 1698, 1638, 1610, 1508, 1490, 1437, 1250, 1220 cm$^{-1}$; NMR (CDCl$_3$, δ) 2.04 (s, 3H), 2.33 (ddd, 1H, J=14, 9, 5 Hz), 3.14 (bd, 1H, J=14 Hz), 3.74-3.98 (m, 5H), 4.22 (bd, 1H, J=9 Hz), 5.32 (m, 1H), 6.97 (s, 1H), 7.42-7.78 (m, 4H), 8.22-8.30 (m, 2H), 8.61 (s, 1H); [α]$_D^{24}$=+233° (C=0.43, CH$_3$OH).

The by-product was shown to be O$^2$,N$^{10}$-diacetylated product, and this material was treated with saturated NaHCO$_3$ solution to give additional title compound. This material and the mother liquor from the recrystallization above were combined to give 49 mg of additional material (total yield=170 mg, 76%).

Anal. Calc'd for C$_{22}$H$_{20}$N$_2$O$_7$.0.5H$_2$O: C, 60.97; H, 4.88; N, 6.46 Found: C, 61.20; H, 4.30; N, 6.19.

G.
2(S),11a(S)-1,2,3,10,11,11a-Hexahydro-2-acetoxy-8-benzoyloxy-7-methoxy-5H-pyrrolo-[2,1-c][1,4]benzodiazepin-5-one-11-thione (10)

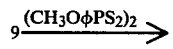

-continued

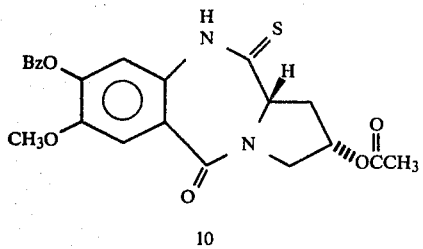

A solution of amide intermediate 9 (240 mg, 0.57 mmol) and 126 mg (0.31 mmol) of 2,4-bis(4-methoxyphenyl)-1,3-dithia-2,4-diphosphetane-2,4-disulfide (Lawesson's reagent) in 25 ml of benzene was refluxed under $N_2$ for 30 minutes. After an additional 126 mg of Lawesson's reagent was added, refluxing was continued for 30 minutes. The residue obtained after evaporation of the solvent was chromatographed on silica gel (0.5% $CH_3OH\text{-}CH_2Cl_2$) to give 170 mg (68% yield) of the title compound. An analytical sample was prepared by recrystallization from $CH_2Cl_2$-ether: mp 238°–240° C.; IR(KBr) 1750, 1648, 1630, 1600, 1508, 1440, 1255, 1060 cm$^{-1}$; NMR(CDCl$_3$, δ) 2.10(s, 3H), 2.48(ddd, 1H, J=14, 9, 6 Hz), 3.06(bd, 1H, J=14 Hz), 3.81–4.16(m, 5H), 4.34(bd, J=9 Hz), 5.30(m, 1H), 7.00(s, 1H), 7.50–7.70(m, 4H), 8.20(m, 2H), 9.82(bs, 1H); $[\alpha]_D^{24}=+367°$ (C=0.29, $CH_3OH$).

Anal. Calc'd for $C_{22}H_{20}N_2O_6S\cdot0.5H_2O$: C, 58.79; H, 4.71; N, 6.23; S, 7.28; Found: C, 58.68; H, 4.49; N, 6.08; S, 7.36.

H.
2(S),11a(S)-1,2,3,11a-Tetrahydro-2,8-dihydroxy-11-methylthio-7-methoxy-5H-pyrrolo-[2,1-c][1,4]benzodiazepin-5-one (11)

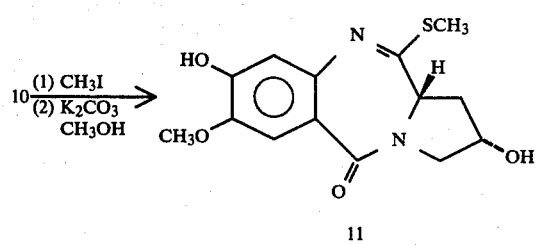

A mixture of thioamide 10 (113 mg, 0.257 mmol), methyl iodide (73 mg, 0.514 mmol) and $K_2CO_3$ (142 mg, 1.03 mmol) in 5 ml of THF was stirred at room temperature overnight. The reaction mixture was filtered through CELITE and the solvent was removed to give 130 mg of foam. This material was dissolved at 0° C. in 5 ml of $CH_3OH$ saturated with $K_2CO_3$. After 1 hour of stirring at 0° C., the solution was carefully neutralized with 0.1 N HCl solution. After the solvents were evaporated under reduced pressure, the residue was extracted with 10% $CH_3OH\text{-}CH_2Cl_2$ to give 79 mg (100% yield) of the title compound: IR(KBr) 3410, 1585, 1496, 1450, 1430, 1275 cm$^{-1}$; NMR(CDCl$_3$+CD$_3$OD, δ) 2.24–2.82(m, 5H), 3.54(d, 1H, J=5 Hz), 3.66–4.20(m, 6H), 4.30–4.58(m, 1H), 6.57(s, 1H), 7.40(s, 1H); mass spectrum (70 eV) m/e (relative intensity), 308(16), 275(9), 261(6), 222(20), 208(100).

I.
2(S),11(R),11a(S)-1,2,3,10,11,11a-Hexahydro-2,8-dihydroxy-7,11-dimethoxy-5H-pyrrolo-[2,1-c][1,4]benzodiazepin-5-one (BBM-2040A)

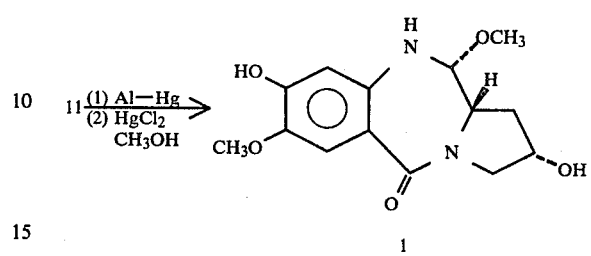

Thioimino ether 11 (72 mg, 0.23 mmol) was dissolved in 10 ml THF and 1 ml of saturated $KH_2PO_4$ solution. Aluminum amalgum prepared by the method of Keck et al[1] (62 mg of aluminum foil, 2.3 mmol) was added at 0° C. The resulting mixture was stirred at 0° C. under a static nitrogen atmosphere for 16 hours. At the end of this period, $Na_2SO_4$ was added to the reaction mixture and the solution was filtered through CELITE. The residue was washed with 10% $CH_3OH\text{-}CH_2Cl_2$. The combined filtrate was evaporated to give a colorless foam. This material was dissolved in 2 ml of $CH_3OH$ and treated at 0° C. with 1.2 ml of 0.1 N methanolic $HgCl_2$ solution. The precipitate was filtered off and the solvent was evaporated. The residue was chromatographed by a silica gel TLC at 4° C. (10% $CH_3OH\text{-}CH_2Cl_2$, two developments). Extraction of the major band gave 33 mg (49% yield) of a colorless amorphous solid 1 whose TLC behavior was identical to that of BBM-2040A. An analytical sample obtained by crystallization from $CH_3OH$: mp 162°–164° C.; IR(KBr) 3380, 1630, 1595, 1565, 1520, 1445 cm$^{-1}$; NMR (pyridine-d$_5$, δ) 2.20–2.78(m, 2H), 3.31(s, 3H), 3.76(s, 3H), 4.00–4.22(m, 2H), 4.34–4.60(m, 2H), 4.76(d, 1H, J=6 Hz), 6.32(d, 1H, J=7 Hz), 6.90(s, 1H), 7.93(d, 1H, J=6 Hz), 8.20(s, 1H), 11.70(bs, 1H); $[\alpha]_D^{24}=+335°$ (C=0.083 pyridine); observed mass 262.0954 (calc'd for BBM-2040A-$CH_3OH$, 262.0952).

[1]Syn. Comm. 9: 281–286, 1979

The second band gave 11 mg (18% yield) of 2(R),11a(S)-1,2,3,10,11,11a-hexayhydro-2,8-dihydroxy-7-methoxy-5H-pyrrolo [2,1-c][1,4]benzodiazepin-5-one, an over-reduction product: IR(KBr) 3380, 1630, 1595, 1565, 1510, 1440 cm$^{-1}$; NMR (CDCl$_3$+CD$_3$OD, δ) 1.84(dt, 1H, J=14, 4 Hz), 2.23–2.58(m, 1H), 3.50–4.12(m, 7H), 4.30–4.60(m, 2H), 6.17(s, 1H), 7.46(s, 1H); mass spectrum (70 eV) m/e (relative intensity), 264(100), 244(82), 179(45), 164(53).

We claim:

1. A process for the preparation of a compound of the formula

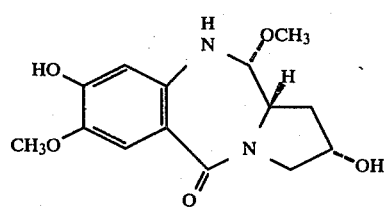

which comprises the steps of (1) coupling a (lower)alkyl ester of trans-4-hydroxy-L-proline in an inert solvent with an acylating derivative of an acid of the formula

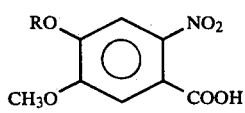

II wherein R is a conventional phenolic hydroxyl protecting group to produce an intermediate of the formula

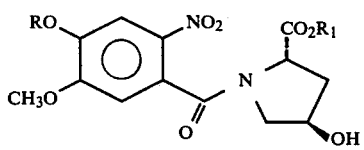

III wherein $R_1$ is (lower)alkyl and R is as defined above;

(2) selectively reducing the nitro group of intermediate III to produce an intermediate of the formula

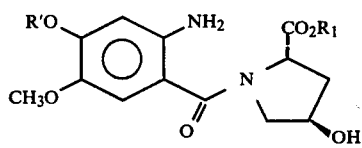

IV wherein R' is hydrogen or a conventional phenolic hydroxyl protecting group and $R_1$ is as defined above;

(3) cyclizing intermediate IV by heating in an inert solvent or by treatment with aqueous acid to produce an intermediate of the formula

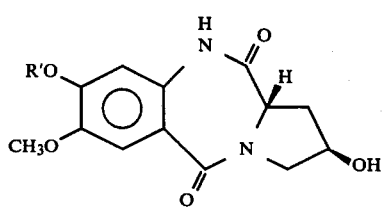

V wherein R' is as defined above;

(4) in the case where R' in intermediate V is hydrogen, converting intermediate V to the corresponding intermediate of the formula

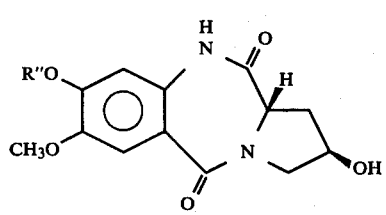

Va wherein R" is a conventional phenolic hydroxyl protecting group;

(5) oxidizing the C-2 hydroxyl group of intermediate V or Va having the C-8 hydroxyl group protected with a conventional phenolic hydroxyl protecting group so as to produce an intermediate of the formula

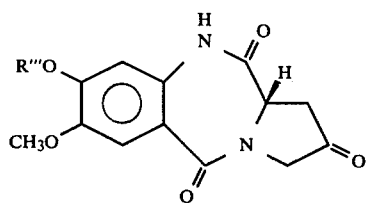

VI wherein R''' is R' or R";

(6) selectively reducing the C-2 keto group of intermediate VI to produce the C-2 α-hydroxy isomer of the formula

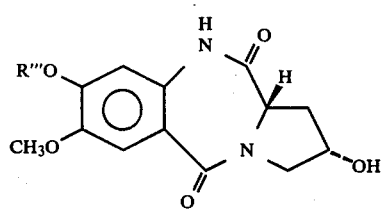

VII wherein R''' is as defined above;

(7) converting intermediate VII to the corresponding intermediate of the formula

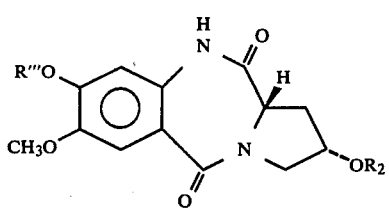

VIII wherein $R_2$ is a conventional hydroxyl protecting group and R''' is as defined above;

(8) reacting amide intermediate VIII with phosphorous pentasulfide or 2,4-bis(4-methoxyphenyl)-1,3-dithia-2,4-diphosphetane-2,4-disulfide in an inert organic solvent to produce the thioamide intermediate of the formula

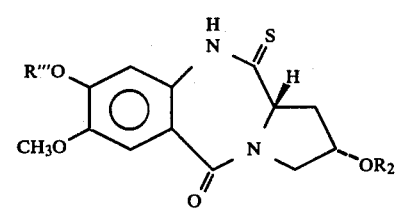

IX wherein $R_2$ and R''' are as defined above;

(9) reacting intermediate IX with a (lower)alkyl halide or (lower)alkoxonium salt in an inert organic solvent and in the presence of base to produce the thioiminoether intermediate of the formula

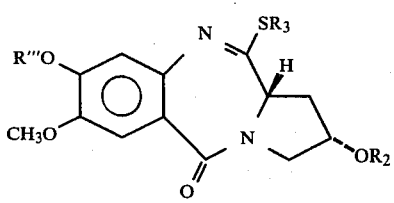

wherein R₃ is (lower)alkyl and R₂ and R'''' are as defined above;

(10) optionally removing the C-2 and C-8 hydroxyl protecting groups of intermediate X to form an intermediate of the formula

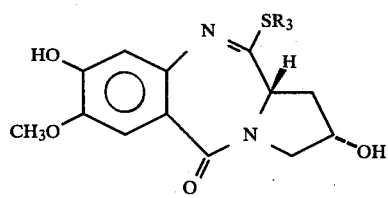

wherein R₃ is as defined above;

(11) selectively reducing the thioiminoether moiety of intermediate XI or intermediate X in an inert solvent to produce a thiocarbinolamine intermediate of the formula

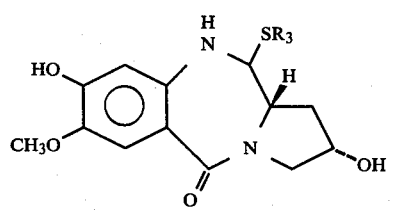

or

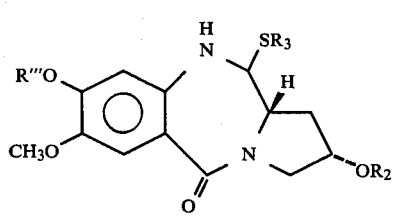

wherein R₃, R and R₂ are as defined above; and

(12) reacting intermediate XII or XII' with a mercuric salt in methanol to form the carbinolamine product of the formula

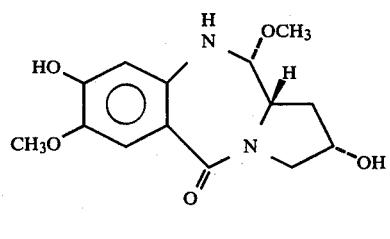

or

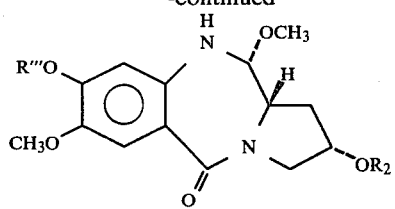

wherein R₂ and R'''' are as defined above; and, when the product obtained is compound I', removing the hydroxyl protecting groups R₂ and R'''' from intermediate I' so as to form the desired deprotected product I.

2. The process according to claim 1 which includes the further step of treating the methanol-adduct product I with pyridine to form the corresponding desmethanol antibiotic of the formula

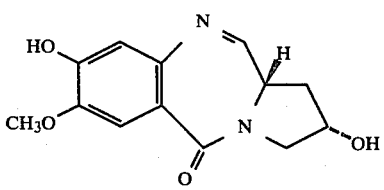

3. The process according to claim 1 or claim 2 wherein the reducing agent used in step (11) is aluminum amalgam.

4. The process according to claim 1 or claim 2 wherein (a) in step (1) a (lower)alkyl ester of trans-4-hydroxy-L-proline is coupled in an inert solvent and in the presence of base with an acylating agent of the formula

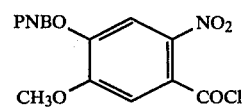

wherein PNB represents p-nitrobenzyl;

(b) in step (2) the reduction is carried out by catalytic hydrogenation;

(c) in step (3) the cyclization is carried out by heating in an inert solvent at a temperature in the range of about 50° to 150° C.;

(d) in step (4) the C-8 hydroxy group of intermediate V is protected by a benzoyl group;

(e) the oxidizing agent in step (5) is Jones reagent;

(f) the selective reduction step (6) is carried out using a metal hydride reducing agent;

(g) the C-2 hydroxy group of intermediate VII is protected in step (7) by an acetyl group;

(h) the thiation reaction step (8) is carried out with 2,4-bis(4-methoxyphenyl)-1,3-dithia-2,4-diphosphetane-2,4-disulfide;

(i) the alkylation step (9) is carried out using methyl iodide in tetrahydrofuran or triethyloxonium tetrafluoroborate in methylene chloride;

(j) the benzoyl and acetyl hydroxyl protecting groups of intermediate X are removed in step (10) by treatment with mild base; and (k) the selective reduction step (11) is carried out using aluminum amalgam as the reducing agent in an aqueous ether solvent.

5. A process for the preparation of a compound of the formula

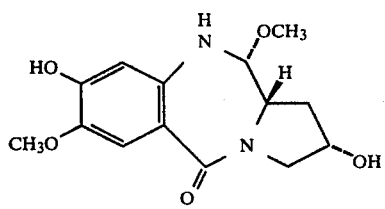

which comprises the steps of
(a) reacting an amide derivative of the formula

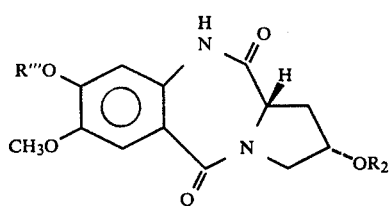

wherein R''' is a conventional phenolic hydroxyl protecting group and R₂ is a conventional hydroxyl protecting group with phosphorous pentasulfide or 2,4-bis(4-methoxyphenyl)-1,3-dithia-2,4-diphosphetane-2,4-disulfide in an inert organic solvent to produce the thioamide intermediate of the formula

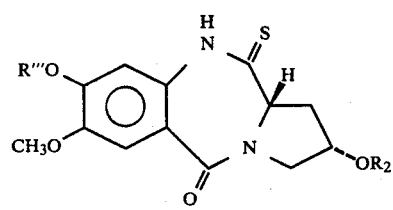

wherein R₂ and R''' are as defined above;
(b) reacting intermedate IX with a (lower)alkyl halide or (lower)alkoxonium salt in an inert organic solvent and in the presence of base to produce the thioiminoether intermediate of the formula

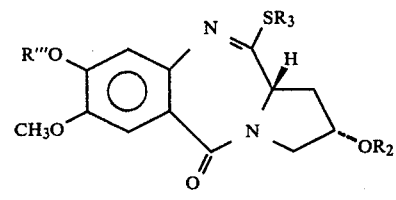

wherein R₃ is (lower)alkyl and R₂ and R''' are as defined above;
(c) optionally removing the C-2 and C-8 hydroxyl protecting groups of intermediate X to form an intermediate of the formula

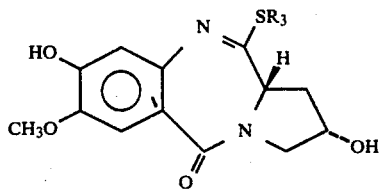

wherein R₃ is as defined above;
(d) selectively reducing the thioiminoether moiety of intermediate X or intermediate XI in an inert solvent to produce a thiocarbinolamine intermediate of the formula

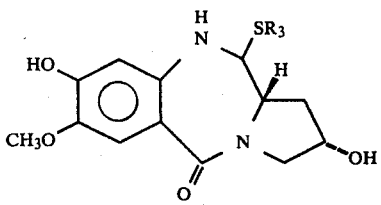

or

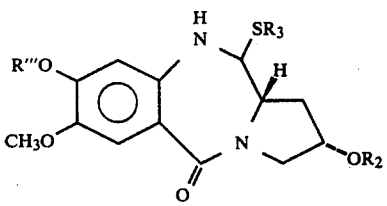

wherein R₃, R and R₂ are as defined above; and
(e) reacting intermediate XII or XII' with a mercuric salt in methanol to form the carbinolamine product of the formula

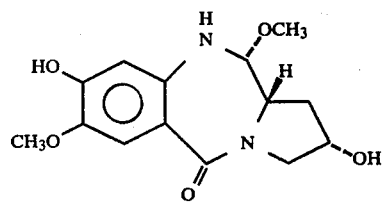

or

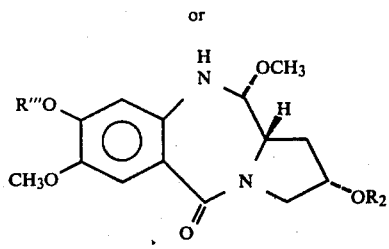

wherein R₂ and R''' are as defined above; and, when the product obtained is compound I', removing the hydroxyl protecting groups R₂ and R''' from intermediate I' so as to form the desired deprotected product I.

6. The process according to claim 5 which includes the further step of treating the methanol-adduct product I with pyridine to form the corresponding desmethanol antibiotic of the formula

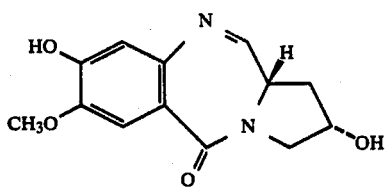

XIII

7. The process according to claim 5 or claim 6 wherein the reducing agent used in step (d) is aluminum amalgam.

8. The process according to claim 5 or claim 6 wherein (1) in step (a) an amide derivative of the formula

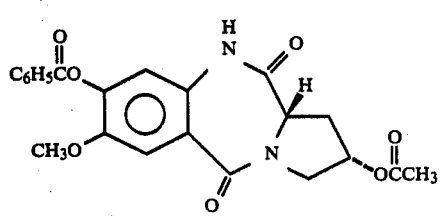

is reacted with 2,4-bis(4-methoxyphenyl)-1,3-dithia-2,4-diphosphetane-2,4-disulfide to form an intermediate of the formula

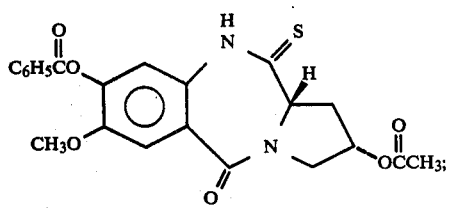

(2) in step (b) the alkylation step is carried out using methyl iodide in tetrahydrofuran or triethyloxonium tetrafluoroborate in methylene chloride;

(3) in step (c) the benzoyl and acetyl hydroxyl protecting groups are removed by treatment with mild base; and (4) in step (d) the selective reduction step is carried out using aluminum amalgam as the reducing agent in an aqueous ether solvent.

9. A process for the preparation of an intermediate of the formula

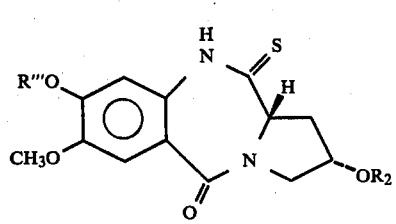

wherein R''' is a conventional phenolic hydroxyl protecting group and $R_2$ is a conventional hydroxyl protecting group, which comprises reacting an amide intermediate of the formula

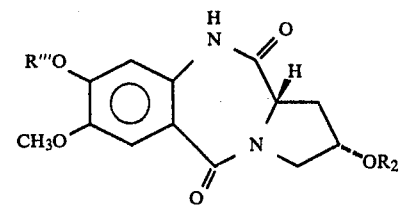

wherein R''' and $R_2$ are as defined above with phosphorous pentasulfide or 2,4-bis(4-methoxyphenyl)-1,3-dithia-2,4-diphosphetane-2,4-disulfide in an inert solvent.

10. The process according to claim 9 wherein the reaction is carried out using 2,4-bis(4-methoxyphenyl)-1,3-dithia-2,4-diphosphetane-2,4-disulfide.

11. A process for the preparation of an intermediate of the formula

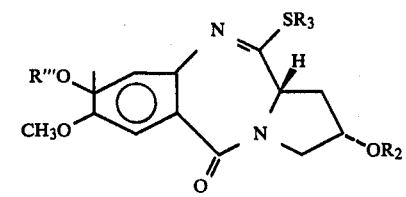

wherein $R_3$ is (lower)alkyl, R''' is a conventional phenolic hydroxyl protecting group and $R_2$ is a conventional hydroxyl protecting group, which comprises reacting an intermediate of the formula

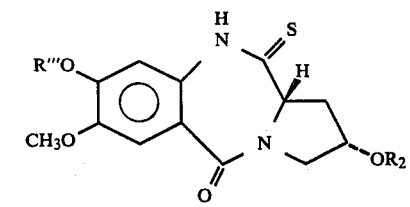

wherein R''' and $R_2$ are as defined above with a (lower)alkyl halide or (lower)alkoxonium salt in an inert organic solvent and in the presence of base.

12. The process according to claim 11 wherein the alkylation step is carried out using methyl iodide in tetrahydrofuran or triethyloxonium tetrafluoroborate in methylene chloride.

13. A process for the preparation of an intermediate of the formula

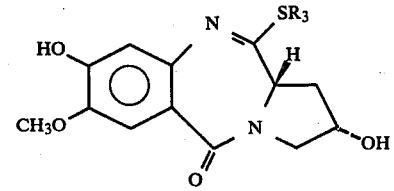

wherein $R_3$ is (lower)alkyl, which process comprises removing the C-2 and C-8 hydroxyl protecting groups of an intermediate of the formula

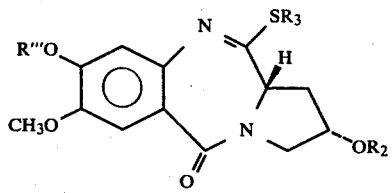

wherein R''' is a conventional phenolic hydroxyl protecting group, $R_2$ is a conventional hydroxyl protecting group and $R_3$ is as defined above.

14. An intermediate of the formula

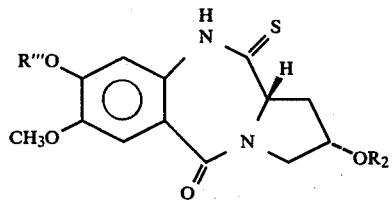

wherein $R_2$ represents a conventional hydroxyl protecting group and R''' represents a conventional phenolic hydroxyl protecting group.

15. An intermediate according to claim 14 wherein R''' is benzoyl and $R_2$ is acetyl.

16. An intermediate of the formula

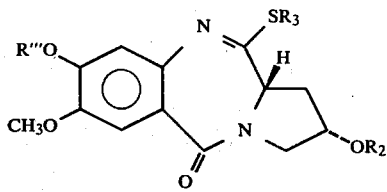

wherein $R_3$ is (lower)alkyl, R''' is a conventional phenolic hydroxyl protecting group and $R_2$ is a conventional hydroxyl protecting group.

17. An intermediate according to claim 16 wherein $R_3$ is methyl, R''' is benzoyl and $R_2$ is acetyl.

18. An intermediate of the formula

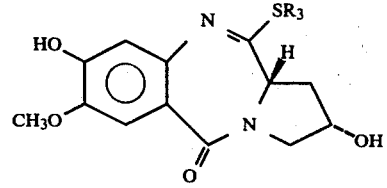

wherein $R_3$ is (lower)alkyl.

19. An intermediate according to claim 18 wherein $R_3$ is methyl.

* * * * *

UNITED STATES PATENT AND TRADEMARK OFFICE
CERTIFICATE OF CORRECTION

PATENT NO.   : 4,427,587
DATED        : January 24, 1984
INVENTOR(S)  : Takushi Kaneko; Henry S.L. Wong It is certified that error appears in the above-identified patent and that said Letters Patent are hereby corrected as shown below:

In Claim 11, the structural formula should read

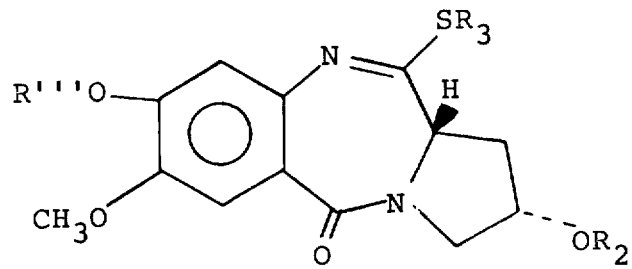

Signed and Sealed this

Twenty-fourth Day of April 1984

[SEAL]

Attest:

Attesting Officer

GERALD J. MOSSINGHOFF
Commissioner of Patents and Trademarks